(12) United States Patent
Otterbein et al.

(10) Patent No.: US 7,691,416 B2
(45) Date of Patent: Apr. 6, 2010

(54) METHODS OF TREATING VASCULAR DISEASE

(75) Inventors: Leo E. Otterbein, Beverly, MA (US); Augustine M. Choi, Pittsburgh, PA (US); Fritz H. Bach, Manchester, MA (US); Brian Zuckerbraun, Pittsburgh, PA (US)

(73) Assignees: Beth Israel Deaconess Medical Center, Inc., Boston, MA (US); University of Pittsburgh of the Commonwealth System of Higher Education, Pittsburgh, PA (US)

( * ) Notice: Subject to any disclaimer, the term of this patent is extended or adjusted under 35 U.S.C. 154(b) by 191 days.

(21) Appl. No.: 12/050,826

(22) Filed: Mar. 18, 2008

(65) Prior Publication Data

US 2008/0167609 A1    Jul. 10, 2008

Related U.S. Application Data

(62) Division of application No. 10/367,277, filed on Feb. 13, 2003, now Pat. No. 7,364,757.

(60) Provisional application No. 60/356,718, filed on Feb. 13, 2002.

(51) Int. Cl.
*A61K 33/00* (2006.01)
*C10B 31/18* (2006.01)
*A61M 16/00* (2006.01)

(52) U.S. Cl. ............... 424/699; 423/418.2; 128/204.18

(58) Field of Classification Search ................ 424/699; 423/418.2; 128/204.18
See application file for complete search history.

(56) References Cited

U.S. PATENT DOCUMENTS

| | | |
|---|---|---|
| 4,053,590 A | 10/1977 | Bonsen et al. |
| 4,264,739 A | 4/1981 | Grabner et al. |
| 4,923,817 A | 5/1990 | Mundt |
| 4,979,939 A | 12/1990 | Shiber |
| 5,084,380 A | 1/1992 | Carney |
| 5,180,366 A | 1/1993 | Woods |
| 5,240,912 A | 8/1993 | Todaro |
| 5,293,875 A | 3/1994 | Stone |
| 5,449,665 A | 9/1995 | Sollevi |
| 5,476,764 A | 12/1995 | Bitensky |
| 5,498,421 A | 3/1996 | Grinstaff et al. |
| 5,588,962 A | 12/1996 | Nicholas et al. |
| 5,632,162 A | 5/1997 | Billy |
| 5,664,563 A | 9/1997 | Schroeder et al. |
| 5,709,874 A | 1/1998 | Hanson et al. |
| 5,731,326 A | 3/1998 | Hart et al. |
| 5,763,431 A | 6/1998 | Jackson |
| 5,792,325 A | 8/1998 | Richardson, Jr. |
| 5,882,674 A | 3/1999 | Herrmann et al. |
| 5,885,621 A | 3/1999 | Head et al. |
| 5,914,316 A | 6/1999 | Brown et al. |
| 5,985,307 A | 11/1999 | Hanson et al. |
| 6,066,333 A | 5/2000 | Willis et al. |
| 6,069,132 A | 5/2000 | Revanker et al. |
| 6,203,991 B1 | 3/2001 | Nabel et al. |
| 6,251,418 B1 | 6/2001 | Ahern et al. |
| 6,313,144 B1 | 11/2001 | McCullough et al. |
| 6,316,403 B1 | 11/2001 | Pinsky et al. |
| 6,409,716 B1 | 6/2002 | Sahatjian et al. |
| 6,436,365 B2 | 8/2002 | Dinkelborg et al. |
| 6,450,989 B2 | 9/2002 | Dubrul et al. |
| 6,508,784 B1 | 1/2003 | Shu |
| 6,508,787 B2 | 1/2003 | Erbel et al. |
| 7,364,757 B2 * | 4/2008 | Otterbein et al. ............ 424/699 |
| 2003/0009127 A1 | 1/2003 | Trescony et al. |
| 2003/0064114 A1 | 4/2003 | Motterlini et al. |
| 2003/0068387 A1 | 4/2003 | Buelow et al. |
| 2004/0067261 A1 | 4/2004 | Haas et al. |
| 2004/0197271 A1 | 10/2004 | Kunka et al. |
| 2005/0048133 A1 | 3/2005 | Pinsky et al. |
| 2005/0215468 A1 | 9/2005 | Bar-Or et al. |
| 2005/0250688 A1 | 11/2005 | Pinsky et al. |
| 2006/0003922 A1 | 1/2006 | Bach et al. |

FOREIGN PATENT DOCUMENTS

| | | |
|---|---|---|
| FR | 2 816 212 | 5/2002 |
| JP | 56079957 A | 6/1981 |
| WO | WO 94/22482 | 10/1994 |
| WO | WO 95/35105 | 12/1995 |
| WO | WO 98/08523 | 3/1998 |
| WO | WO 98/13058 | 4/1998 |
| WO | WO 99/47512 | 9/1999 |
| WO | WO 99/49880 | 10/1999 |
| WO | WO 02/09731 | 2/2002 |
| WO | WO 02/092075 | 11/2002 |
| WO | WO 03/000114 | 1/2003 |
| WO | WO 2004/004817 | 1/2004 |

OTHER PUBLICATIONS

Abidin et al., "The Combined Effect of Carbon Monoxide and Normobaric Hyperoxia on Animals", Kosmicheskaya Biologiya I Aviakosmicheskaya Meditsina 6: 63-67 (1978).
Allred et al., "Effects of Carbon Monoxide on Myocardial Ischemia," Environmental Health Perspectives 91:89-132 (1991).
Appel et al., "The pig as a source of Cardiac xenografts," J. Card. Surg. 16:345-56, (2001).
Arita et al., "Prevention of Primary Islet Isograft Nonfunction in Mice with Pravastatin," *Transplantation* 65:1429-33 (1998).
Arnush et al., "IL-1 Produced and Released Endogenously within Human Islets Inhibits β Cell Function," J. Clin Invest. 102:516-26 (1998).
Bach et al., "Accommodation of vascularized xenografts: Expression of "protective genes" by donor endothelial cells in a host Th2 cytokine environment," *Nature Med*. 3:196-204 (1997).

(Continued)

*Primary Examiner*—Raymond J Henley, III
(74) *Attorney, Agent, or Firm*—Fish & Richardson P.C.

(57) ABSTRACT

The present invention relates to a method of treating patients suffering from, or at risk for, intimal hyperplasia and/or arteriosclerosis. The treatment includes administering a pharmaceutical composition that includes carbon monoxide to the patient.

6 Claims, 18 Drawing Sheets

OTHER PUBLICATIONS

Bach, "Heme oxygenase-1 as a protective gene," Wien. Klin. Wochenschr. 114(Suppl):4:1-3 (2002).

Baim and Grossman, "Treatment of Coronary Stenoses and Occlusions with Coronary Angioplasty," Harrison's Principles of Internal Medicine, 13th Ed., vol. 1, 193:986-87 (1994).

Bathoorn et al., "Anti-inflammatory effects of inhaled carbon monoxide in patients with COPD: a pilot study," Eur. Respir. J. 0:09031936.00163206v1 (Aug. 22, 2007).

Bentley et al., "Successful Cardiac Transplantation with Methanol or Carbon Monoxide-Poisoned Donors," Thorac Surg 71(4):1194-7 (2001).

Berney et al., "Islet cell transplantation: the future?" Langenbeck's Arch. Surg. 385: 373-8 (2000).

Billiar, "The diverging roles of carbon monoxide and nitric oxide in resuscitated hemorrhagic shock," Crit. Care Med. 27:2842-3 (1999).

Bracho et al., "Carbon Monoxide Protects against Organ Injury in Hemorrhagic Shock/Resuscitation," Journal of Surgical Research, 107:270, (2002), Abstract.

Brouard et al., "Carbon monoxide generated by Heme Oxygenase-1 (HO-1) suppresses endothelial cell apoptosis via activation of the p38 mitogen activated protein kinase (MAPK) pathway," Acta Haematologica 103(Suppl 1):64, (2000), Abstract.

Brouard et al., "Carbon Monoxide Generated by Heme Oxygenase-1 Suppresses Endothelial Cell Apoptosis," J. Exp Med 192(7):1015-25 (2000).

Brouard et al., "Heme oxygenase-1-derived carbon monoxide requires the activation of transcription factor NF-kappa B to protect endothelial cells from tumor necrosis factor-alpha-mediated apoptosis," J. Biol. Chem., 277(20):17950-17961, (2002).

Brouard et al., "Molecular mechanism underlying the anti-apoptotic effect of Heme oxygenase-1 derived carbon monoxide," Xenotransplantation, 8(Suppl 1): p. 22 (2001).

Brown et al., "In vivo binding of carbon monoxide to cytochrome $c$ oxidase in rat brain", American Physiological Society, pp. 604-610 (1990).

Calabrese et al., "Carbon Monoxide (CO) Prevents Apoptotic Events Related to Ischemia/Reperfusion (IR) Injury in an hDAF Pig-to-Primate Xenotransplantation Model," Xenotransplantation 10:488, (2003), Abstract.

Campbell, "Living At Very High Altitudes", The Lancet 1:370-373 (1930).

Campbell, "The Effect of Carbon Monoxide and Other Agents Upon the Rate of Tumour Growth", J Pathology & Bacteriology 35:379-394 (1932).

Campell, "Cancer of Skin and Increase in Incidence of Primary Tumours of Lung in Mice Exposed to Dust Obtained from Tarred Roads", Brit. J Exper. Pathol. XV(5):24, 289-294 (1934).

Cantrell et al., "Low-Dose Carbon Monoxide Does Not Reduce Vasoconstriction in Isolated Rat Lungs", Experimental Lung Research 22:21-32 (1996).

Carbon Monoxide Poisoning—Symptoms; http://my.webmd.com/hw/home_health/aa7304.asp;retrieved Jul. 11, 2005.

Carbon Monoxide Poisoning—Symptoms; http://my.webmd.com/hw/home_health/aa7326.asp; retrieved Jul. 11, 2005.

Carbon Monoxide Poisoning—Symptoms; http://my.webmd.c.orn/hw/home_health/aa7304.asp; retrieved Jul. 11, 2005.

Carbon Monoxide Poisoning—What Happens; http://my.webmd.com/hw/home_health/aa7326.asp;retrieved Jul. 11, 2005.

Carbon Monoxide to Prevent Lung Inflammation, http://www.clinicaltrials.gov/ct/show/NCT00094406?order=2 (website visited by Applicant on Aug. 28, 2006).

Cardell et al., "Bronchondilatation in vivo by carbon monoxide, a cyclic GMP related messenger", British J. of Pharmacology 124:1065-1068 (1998).

Carlsson et al., "Measurements of Oxygen Tension in Native and Transplanted Rat Pancreatic Islets," Diabetes 47:1027-32 (1998).

Carraway at al., "Induction of ferritin and heme oxygenase-1 by endotoxin in the lung", Am J Physiol Lung Cell Mol Physiol 275:L583-592 (1998).

Cecil Textbook of Medicine (21$^{st}$ Ed. 2000) 1:273-279, 357-372, 387-419, 425-427, 436-448, 466-475, 507-512, 1060-1074.

Cecil Textbook of Medicine (21$^{st}$ Ed. 2000) 2:1492-1499, 2042-2047, 2079-2081.

Chapman and Choi, "Exhaled monoxides as a pulmonary function test: use of exhaled nitric oxide and carbon monoxide," Clin Chest Med. 22:817-836 (2001).

Chapman et al., "Carbon Monoxide Attenuates Aeroallergen-induced Inflammation in Mice", Am. J. Physiol. Lung Cell Mol Physiol. 281:L209-L216 (2001).

Chapman et al., "Exogenous Carbon Monoxide Attenuates Aeroallergen-induced Eosinophilic Inflammation in Mice", J Respiratory Critical Care Med 159(3):A218 (1999).

Chin et al., "Transcriptional regulation of the HO-1 gene in cultured macrophages exposed to model airborne particulate matter," Am. J. Physiol. Lung Cell. Mol. Physiol., 284(3):L473-L480, (2003).

Choi and Otterbein, "Emerging role of carbon monoxide in physiologic and pathophysiologic states." Antioxid. Redox Signal. 4:227-228 (2002).

Choi et al., ""Therapeutic" carbon monoxide may be a reality soon," Am. J. Respir. Crit. Care Med., 171(11):1318-1319, (2005).

Choi et al., "Heme Oxygenase-1: Function, Regulation, and Implication of a Novel Stress-inducible Protein in Oxidant-induced Lung Injury", Am. J. Respir. Cell Mol. Biol. 15:9-19 (1996).

Choi, "Heme Oxygenase-1 Protects the Heart," Circulation Research 89:105-107 (2001).

Christodoulides et al., "Vascular Smooth Muscle Cell Heme Oxygenases Generate Guanylyl Cyclase-Stimulatory Carbon Monoxide," Circulation 97:2306-9 (1995).

Clayton et al., "Inhaled carbon monoxide and hyperoxic lung injury in rats," Am. J. Physiol. Lune Cell Mol. Physiol. 281:L949-57 (2001).

Colorectal Cancer Treatment: an Overview (2000) author unknown.

Corbett et al., "Nitric oxide mediates cytokine-induced inhibition of insulin secretion by human islets of Langerhans," Proc. Natl. Acad. Sci USA 90:1731-5 (1993).

Cozzi et al., "Donor Preconditioning with Carbon Monoxide (CO) in Pig-to-Primate Xenotransplantation," Xenotransplantation 10:528, (2003), Abstract.

Crapo et al., "Single-breath carbon monoxide diffusing capacity," Clin. Chest Med., 22:637-649, (2001).

Davidson et al., "Inflammatory Modulation and Wound Repair" J Investigative Dermatology xi-xii (2003).

Deng et al., "Carbon Monoxide Potentiates Cerulein-Induced Pancreatitis in Chronic Alcohol-Fed Rats," Gastroenterology, 124(4):A618-19, (2003), Abstract.

Dioum et al., "NPAS2: A Gas-Responsive Transcription Factor", Sciencexpress/www.sciencexpress.org/21 November 2002/pages 1-6/10.1126/science.1078456.

Dolinay et al., "Can Inhalation Carbon Monoxide be utilized as a therapeutic modality in human diseases?", pp. 203-236 in Breath Analysis for Clinical Diagnosis and Therapeutic Monitoring, Amann and Smith, eds., World Scientific Publishing Company (2004).

Dolinay et al., "Inhaled carbon monoxide confers antiinflammatory effects against ventilator-induced lung injury," Am. J. Respir. Crit. Care Med., 170:613-20 (2004).

Donnelly et al., "Expression of Heme-Oxygenase in Human Airway Primary Epithelial Cells", J Respiratory Critical Care Med 159(3):A218 (1999).

Dyck et al., "Carbon Monoxide (CO) Attenuates Lipopolysaccharide (LPS)-Induced Cytokine Expression of IL-6," Acta Haematologica 103(Suppl 1):64, (2000), Abstract.

Farrugia and Szurszewski, "Heme oxygenase, carbon monoxide, and interstitial cells of Cajal," Microsc. Res. Tech. 47:321-4, (1999).

Favory et al., "Myocardial Dysfunction and Potential Cardiac Hypoxia in Rats Induced by Carbon Monxide Inhalation," Am. J. Respir. Crit. Care Med. 174:320-25 (2006).

Friebe et al., "YC-1 Potentiates Nitic Oxide- and Carbon Monoxide-Induced Cyclic GMP Effects in Human Platelets", Molecular Pharmacology 54: 962-967 (1998).

Fujita et al., "Paradoxical rescue from ischemic lung injury by inhaled carbon monoxide driven by derepression of fibrinolysis," Nature Medicine 7:598-604 (2001).

Gaine et al., "Induction of Heme Oxygenase-1 with Hemoglobin Depresses Vasoreactivity in Rat Aorta," J Vasc Res 36(2):114-9 (1999).

Grau et al., "Effect of Carbon Monoxide Breathing on Hypoxia and Radiation Response in the SCCVII Tumor in vivo", *Int. J. Radiation Oncology Biol. Phys.* 29:449-454 (1994).

Grau et al., "Influence of Carboxyhemoglobin Level on Tumor Growth, Blood Flow, and Radiation Response in an Experimental Model," *Int. J. Radiation Oncology Biol. Phys.* 22:421-424 (1992).

Günther et al., "Carbon monoxide protects pancreatic beta-cells from apoptosis and improves islet function/survival after transplantation," Diabetes, 51(4):994-999, (2002).

Hantson et al., "Organ Transplantation From Victims of Carbon Monoxide Poisoning," *Ann Emerg Med* 27(5):673-4 (1996).

Harrison's Principles of Internal Medicine, (13th edition, vol. 1), Published 1994 by McGraw-Hill, Inc. (NY), pp. 986-987.

Hartsfield and Choi, "Mitogen activated protein kinase (MAPK) is modulated by both endogenous and exogenous carbon monoxide," FASEB Journal 12:A187, 1088, (1998), Abstract.

Hartsfield et al., "Differential signaling pathways of HO-1 gene expression in pulmonary and systemic vascular cells," Am. J. Physiol., 277(6 Pt 1):L1133-L1141, (1999).

Hartsfield et al., "Regulation of heme oxygenase-1 gene expression in vascular smooth muscle cells by nitric oxide," Am. J. Physiol., 273(5 Pt 1):L980-988, (1997).

Hartsfield, "Cross talk between carbon monoxide and nitric oxide," Antioxid. Redox Signal. 4:301-307 (2002).

Hartsfield, "Targeted Overexpression of Heme Oxygenase-1 (HO-1) Attenuates Hypoxia-Induced Right Ventricular Hypertrophy," FASEB Journal 13:A827, (1999), Abstract.

Hayes et al., "A Review of Modern Concepts of Healing of Cutaneous Wounds," J. Dermatol. Surg. Oncol. 3(2):188-93 (1977).

Hebert et al., "Transplantation of Kidneys from a Donor with Carbon Monoxide Poisoning," New Engl J Med 326(23):1571 (1992).

Horvath et al., "'Haemoxygenase-1 induction and exhaled markers of oxidative stress in lung diseases', summary of the ERS Research Seminar in Budapest, Hungary, Sep. 1999," Eur. Respir. J., 18(2):420-430, (2001).

Huizinga, Jan D., "Physiology and Pathophysiology of the Interstitial Cell of Cajal: From Bench to Bedside: II. Gastric motility: lessons fron-mutant mice on slow waves and innervation," Am. J. Physiol. 281:1129-1134, (2001).

Iberer et al., "Cardiac Allograft Harvesting after Carbon Monoxide Poisoning. Report of a Sucessful Orthotopic Heart Transplantation," *J Heart Lung Transplant* 12(3):499-500 (1993).

Johnson et al., "Relationships between drug activity in NCI preclinical in vitro and in vivo models and early clinical trials," Br. J. Cancer 84:1424-31(2001).

Katori et al., "Heme Oxygenase-1 System in Organ Transplantation", *Transplantation* 74(7):905-912 (2002).

Kaufman et al., "Differential Roles of Mac-1$^+$ Cells, and CD4$^+$ and CD8$^+$ T Lymphocytes in Primary Nonfunction and Classic Rejection of Islet Allografts," *J Exp Med*. 172:291-302 (1990).

Koerner et al., "Extended Donor Criteria: Use of Cardiac Allografts after Carbon Monoxide Poisoning," *Transplantation* 63(9):1358-60 (1997).

Kozma et al, "Role of carbon monoxide in heme-induced vasodilation," Eur. J. Pharmacol., 323:R1-2 (1997).

Kyokane et al., "Carbon Monoxide From Heme Catabolism Protects Against Hepatobiliary Dysfunction in Endotoxin-Treated Rat Liver," Gastroenterology 120:1227-40 (2001).

Lacy et al., "Transplantation of Pancreatic Islets," *Ann. Rev. Immunol* 2:183-98 (1984).

Lee et al., "Intestinal Motility and Absorption in Acute Carbon Monoxide Poisoning," Seoul J. Med. 15:95-105 (1974); English translation.

Lee et al., "Regulation of Heme Oxygenase-1 Expression In Vivo and In Vitro in Hyperoxic Lung Injury", *Am. J. Respir. Cell Biol*. 14:556-568 (1996).

Lefer et al., "A Comparison of Vascular Biological Actions of Carbon Monoxide and Nitric Oxide", *Meth Find Exp Clin Pharmacol* 15(9):617-622 (1993).

Leikin et al., "The Toxic Patient as a Potential Organ Donor," *Am J Emerg Med* 12(2):151-4 (1994).

Libby and Poeber, "Chronic Rejection," Immunity 14:387-97 (2001).

Libby et al., "Chronic Rejection," Immunity, 14:387-397 (2001).

Liu et al., "Carbon Monoxide and Nitric Oxide Suppress the Hypoxic Induction of Vascular endothelial Growth Factor Gene via the 5' Enhancer," J. Biol. Chem. 273:15257-15262 (1998).

Liu et al., "Carbon monoxide and nitric oxide suppress the hypoxic induction of vascular endothelial growth factor gene via the 5' enhancer," J. Biol. Chem. 273(24):15257-62 (1998).

Mandrup-Poulsen et al., "Human Tumor Necrosis Factor Potentiates Human Interleukin 1-Mediated Rat Pancreatic β-Cell Cytotoxicity," *J. Immunol* 139:4077-82 (1987).

Mansouri et al., "Alteration of Platelet Aggregation by Cigarette Smoke and Carbon Monoxide," *Thromb Haemost* 48:286-8 (1982).

Maxwell et al., "Studies in Cancer Chemotherapy: XI. The Effect of CO, HCN, and Pituitrin Upon Tumor Growth", Dept. of Cancer Research, Santa Barbara Cottage Hospital, pp. 270-282 (Jan. 30, 1933).

Mayr et al., "Effects of carbon monoxide inhalation during experimental endotoxemia in humans," Am. J. Respir. Crit. Care Med., 171(4):354-360, (2005).

Mayr et al., *Am. J. Respir. Crit. Care Med.*, 171:354-360 (2005).

Mazzola et al., "Carbon monoxide pretreatment prevents respiratory derangement and ameliorates hyperacute endotoxic shock in pigs," FASEB J. 19:2045-2047 (2005).

Meilin et al., Effects of carbon monoxide on the brain may be mediated by nitric oxide, *J Appl Physiol*. 81(3):1078-83 (1996).

Miller et al., "Heme oxygenase 2 is present in interstitial cell networks of the mouse small intestine," Gastroenterology 114(2):239-44, (1998).

Minamino et al., "Targeted expression of heme oxygenase-1 prevents the pulmonary inflammatory and vascular responses to hypoxia", *PNAS* 98(15):8798-8803 (2001).

Modification of Chronic Inflammation by Inhaled Carbon Monoxide in Patients With Stable Chronic Obstructive Pulmonary Disease (COPD), http://www.clinicaltrials.gov/ct/show/NCT00122694?order=1 (website visited by Applicant on Aug. 28, 2006).

Moore et al., "Carbon Monoxide Protects against Intestinal Dysmotility Associated with Small Bowel Transplantation," Gastroenterology 122:A38, (2002), Abstract.

Moore et al., "Carbon Monoxide Suppresses the Development of Ileus Associated with Surgical Manipulation of the Small Intestine," Gastroenterology 122:A61-A62, (2002), Abstract.

Moore et al., "Inhaled Carbon Monoxide Suppresses the Development of Postoperative Ileus in the Murine Small Intestine," Gastroenterology 124:377-91 (2003).

Moore et al., "Pre-treatment with Low Concentrations of Carbon Monoxide (250 TO 75 ppm) for 3 hr prior to Laparotomy Protects Against Postoperative Ileus," Digestive Disease Week abstracts and Itinerary Planner 2003: Abstract No. M1337 (2003).

Mori et al., "Evaluation of hypothermic heart preservation with University of Wisconsin solution in heterotopically and orthotopically transplanted canine hearts," J. Heart Lung Transplant. 13:688-950, (1994).

Morse and Choi, "Heme oxygenase-1: from bench to bedside," Am. J. Respir. Crit. Care Med. 172:660-670 (2005).

Morse et al., "Carbon monoxide-dependent signaling," Crit. Care Med., 30:S12-S17, (2001).

Morse et al., "Suppression of inflammatory cytokine production by carbon monoxide involves the JNK pathway and AP-1," J. Biol. Chem., 278(39):36993-36998, (2003).

Motterlini et al., "Carbon Monoxide-Releasing Molecules: Characterization of Biochemical and Vascular Activities," Circ. Res. 90:17-24 (2002).

Myers, "Cirrhotic cardiomyopathy and liver transplantation," *Liver Transpl* 6(4 Suppl 1):S44-52 (2000).

Nachar at al., "Low-Dose Inhaled Carbon Monoxide Reduces Pulmonary Vascular Resistance During Acute Hypoxemia in Adult Sheep," High Altitude Medicine & Biology 2:377-385 (2001).

Nagata et al., "Destruction of Islet Isografts by Severe Nonspecific Inflammation," Transplant Proc. 22:855-6 (1990).

Nakao et al., "A single intraperitoneal dose of carbon monoxide-saturated ringer's lactate solution ameliorates postoperative ileus in mice," J. Pharmacol. Exp. Ther. 319:1265-75 (2006).

Nakao et al., "Immunomodulatory effects of inhaled carbon monoxide on rat syngeneic small bowel graft motility," Gut 52:1278-85 (2003).

Nakao et al., "Protective effect of carbon monoxide inhalation for cold-preserved small intestinal grafts," Surgery, 134:285-92, (2003).

Ning et al., "TGF-beta1 stimulates HO-1 via the p38 mitogen-activated protein kinase in A549 pulmonary epithelial cells," Am. J. Physiol. Lung Cell. Mol. Physiol., 283(5):L1094-L1102, (2002).

Otterbein et al., "Carbon monoxide suppresses arteriosclerotic lesions associated with chronic graft rejection and with balloon injury," Nature Medicine 9:183-90 (2003).

Otterbein et al., "Carbon monoxide at low concentrations induces growth arrest and modulates tumor growth in mice," Exp. Biol. Med., 228(5):633, (2003), Abstract.

Otterbein et al., "Carbon monoxide has anti-inflammatory effects involving the mitogen-activated protein kinase pathway", *Nature Medicine* 6(4): 422-8 (2000).

Otterbein et al., "Carbon Monoxide Inhibits TNFα-Induced Apoptosis and Cell Growth in Mouse Fibroblasts," American Journal of Respiratory and Critical Care Medicine 159(3 Suppl.):A285 (1999).

Otterbein et al., "Carbon Monoxide Modulates Lipolysaccharide (LPS)-Induced Inflammatory Responses in vivo and in vitro," American Journal of Respiratory and Critical Care Medicine 159(3 Suppl.):A481 (1999).

Otterbein et al., "Carbon monoxide provides protection against hyperoxic lung injury", *The American Physiological Society* L688-L694 (1999).

Otterbein et al., "Carbon monoxide provides protection against hyperoxic lung injury in rats", *J Respiratory Critical Care Med* 159(3):A218 (1999).

Otterbein et al., "Carbon Monoxide, a Gaseous Molecule with Anti-Inflammatory Properties," pp. 133-156 in *Disease Markers in Exhaled Breath*, Marczin et al., eds., Marcel Dekker, Inc., New York, (2003).

Otterbein et al., "Carbon Moxoxide Mediates Anti-Inflammatory Effects Via the P38 Mitogen Activated Protein Kinase Pathway," Acta Haematologica 103: 64, (2000), Abstract.

Otterbein et al., "Carbon Moxoxide Protects Against Oxidant-Induced Lung Injury in Mice Via the p38 Mitogen Activated Protein Kinase Pathway," Acta Haematologica 103:83, (2000), Abstract.

Otterbein et al., "Exogenous administration of heme oxygenase-1 by gene transfer provides protection against hyperoxia-induced lung injury," J. Clin. Invest., 103(7):1047-1054, (1999).

Otterbein et al., "Heme oxygenase: colors of defense against cellular stress," Am. J. Physiol. Lung Cell. Mol. Physiol., 279(6):L1029-L1037, (2000).

Otterbein et al., "Mechanism of hemoglobin-induced protection against endotoxemia in rats: a ferritin-independent pathway", *Am J Physiol Lung Cell Mol Physiol* 272:L268-275 (1997).

Otterbein et al., "Protective effects of heme oxygenase-1 in acute lung injury," Chest. 116:61S-63S, (1999).

Otterbein LE, Choi AMK, "Carbon monoxide at low concentrations causes growth arrest and modulates tumor growth in mice," [Abstract], Am. J. Respir. Crit. Care Med. 163:A476 (2001).

Otterbein, "Anti-Inflammatory Effects of Carbon Monoxide in the Lung," CRISP Data Base National Institute of Health; Doc. No. CRISP/2003HL071797-01A1, (2003).

Otterbein, "Carbon monoxide: innovative anti-inflammatory properties of an age-old gas molecule," Antioxid. Redox Signal., 4:309-319, (2002).

Pannen et al., "Protective Role of Endogenous Carbon Monoxide in Hepatic Microcirculatory Dysfunction after Hemorrhagic Shock in Rats," J. Clin. Invest. 102:1220-1228 (1998).

Paredi et al., "Increased Carbon Monoxide in Exhaled Air of Cystic Fibrosis Patients", *J Respiratory Critical Care Med* 159(3):A218 (1999).

Peek et al., "Extracorporeal Membrane Oxygenation for Adult Respiratory Failure," Chest 112(3)759-64 (1997).

Petrache et al., "Heme oxygenase-1 inhibits TNF-α-induced apoptosis in cultured fibroblasts," *Am. J Physiol. Lung Cell Mol. Physiol.* 287: L312-L319 (2000).

Piantadosi et al., "Production of Hydroxyl Radical in the Hippocampus After CO Hypoxia Hypoxia in the Rat", *Free Radical Biol. & Med.* 22(4):725-732 (1997).

Pileggi et al., "Heme oxygenase-1 induction in islet cells results in protection from apoptosis and improved in vivo function after transplantation," Diabetes, 50(9):1983-1991, (2001).

Pozzoli et al., "Carbon Monoxide as a Novel Neuroendocrine Modulator: Inhibition of Stimulated Corticotropin-Releasing Hormone Release from Acute Rat Hypothalamic Explants," *Endocrinology* 135:2314-2317 (1994).

Rabinovitch et al., "Transfection of Human Pancreatic Islets With an Anti-Apoptotic Gene (*bcl-2*) Protects β-Cells From Cytokine-Induced Destruction," *Diabetes* 48:1223-9, 1999.

Raman et al., "Inhaled carbon monoxide inhibits intimal hyperplasia and provides added benefit with nitric oxide," J. Vasc. Surg. 44:151-158 (2006).

Ramlawi et al., "Inhaled Carbon Monoxide Prevents Graft-Induced Intimal Hyperplasia in Swine," J. Surg. Res. 138:121-127 (2007).

Ringel et al., "Carbon Monoxide-induced Parkinsonism", J. neurol. Sci. 16:245-251 (1972).

Roberts et al., "Successful Heart Transplantation From a Victim of Carbon Monoxide Poisoning," *Ann Emerg Med* 26(5):652-5 (1995).

Ryter and Choi, "Heme Oxygenase-1: Molecular Mechanisms of Gene Expression in Oxygen-Related Stress," Antioxid. Redox Signal. 4:625-632, (2002).

Ryter et al., "Heme oxygenase/carbon monoxide signaling pathways: Regulation and functional significance," Mol. Cell. Biochem., 234-235(1-2):249-63, (2002).

Ryter et al., "Heme oxygenase-1/carbon monoxide: from basic science to therapeutic applications," Physiol. Rev., 86:583-650, (2006).

Ryter et al., "Mitogen Activated Protein Kinase (MAPK) Pathway Regulates Heme Oxygenase-1 Gene Expression by Hypoxia in Vascular Cells," Exp. Biol. Med., 228(5):607, (2003), Abstract.

Ryter et al., "Therapeutic applications of carbon monoxide in lung disease," Curr. Opin. Pharmacol., 6(3):257-262, (2006).

Ryter et al., *Current Opinion in Pharmacology*, 6:257-262 (2006).

Sarady et al., "Carbon monoxide modulates endotoxin-induced production of granulocyte macrophage colony-stimulating factor in macrophages," Am. J. Respir. Cell. Mol. Biol., 27(6):739-745, (2002).

Sarady et al., "Cytoprotection by heme oxygenase/CO in the lung," in *Disease Markers in Exhaled Breath*, Marczin and Yacoub, eds., IDS Press, 346:73-78, (2002).

Sasidhar et al., "Exogenous Carbon Monoxide Attenuates Mitogen Activated Protein Kinase (MAPK) Activation in Rat Pulmonary Artery Endothelial Cells Exposed to Hypoxia," American Journal of Respiratory and Critical Care Medicine. 1999;159(3 Suppl.):A352.

Sass et al., "Heme Oxygenase-1 induction Prevents Apoptotic Liver Damage in Mice," Naunyn-Schmiedeberg's Archives of Pharmacology 367:R78, (2003).

Sato et al., "Carbon monoxide can fully substitute Heme Oxygenase-1 in suppressing the rejection of mouse to rat cardiac transplants," Acta Haematologica, 103(Suppl. 1):87, Abstract 348 (2000).

Sato et al., "Heme oxygenase-1 or carbon monoxide prevents the inflammatory response associated with xenograft rejection," Acta Haematologica, 103(Suppl. 1):87, Abstract 345 (2000).

Sato et al., "Carbon Monoxide Generated by Heme Oxygenase-1 Suppresses the Rejection of Mouse-to-Rat Cardiac Transplants," *J. Immunol.* 166: 4185-4194 (2001).

Schipper et al., "Expression of Hemee Oxygenase-1 in the Senescent and Alzheimer-diseased Brain". *Annals of Neurology* 37(6): 758-68 (1995).

Sethi et al, "Differential modulation by exogenous carbon monoxide of TNF-alpha stimulated mitogen-activated protein kinases in rat pulmonary artery endothelial cells," Antioxid. Redox Signal., 4:241-8, (2002).

Sethi et al., "Differential Effects of Exogenous Carbon Monoxide on TNF-α-Induced Mitogen Activated Protein (MAP) Kinase Signaling Pathway in Rat Pulmonary Artery Endothelial Cells," American Journal of Respiratory and Critical Care Medicine 159(3 Suppl.):A350 (1999).

Seyfried et al., "HO-1 induction protects mice from Immune-mediated liver injury," Naunyn-Schmiedeberg's Archives of Pharmacology 367:R80 (2003).

Shapiro et al., "Islet Transplantation in Seven Patients with Type 1 Diabetes Mellitus Using a Glucocorticoid-Free Immunosuppressive Regimen," *N Engl. J. Med.*, 343:230-8, 2000.

Shennib et al., "Successful transplantation of a lung allograft from a carbon monoxide-poisoning victim," *Heart Lung Transplant* 11(1 Pt 1): 68-71 (1992).

Singhal et al., "Effects of Normobaric Hyperoxia in a Rat Model of Focal Cerebral Ischemia-Reperfusion", *J Cerebral Blood Flow & Medicine* 22:861-868 (2002).

Siow et al., "Heme oxygenase-carbon monoxide signalling pathway in atherosclerosis: anti-atherogenic actions of bilirubin and carbon monoxide?", *Cardiovascular Research* 41:385-394 (1999).

Slebos et al., "Heme oxygenase-1 and carbon monoxide in pulmonary medicine," Respir. Res. 4(7):1-13, (2003).

Smith et al., "Successful Heart Transplantation with Cardiac Allografts Exposed to Carbon Monoxide Poisoning," *Heart Lung Transplant* 11(4 Pt. 1):698-700 (1992).

Soares et al, "Heme oxygenase-1, a protective gene that prevents the rejection of transplanted organs," Immunol. Rev. 184:275-85, (2001).

Soares et al, "Modulation of endothelial cell apoptosis by heme oxygenase-1-derived carbon monoxide," Antioxid. Redox Signal., 4:321-329, (2002).

Soares et al., "Expression of heme oxygenase-1 can determine cardiac xenograft survival," *Nat Med.* 4(9):1073-1077 (1998).

Soares et al., "Heme Oxygenase-1 and/or Carbon Monoxide can Promote Organ Graft Survival," in *Disease Markers in Exhaled Breath*, Marczin and Yacoub, eds., IDS Press, 346:267-273, (2002).

Song et al., "Carbon monoxide induces cytoprotection in rat orthotopic lung transplantation via anti-inflammatory and anti-apoptotic effects," Am. J. Pathol., 163(1):231-242, (2003).

Song et al., "Carbon monoxide inhibits human airway smooth muscle cell proliferation via mitogen-activated protein kinase pathway," Am. J. Respir. Cell. Mol. Biol. 27(5):603-610, (2002).

Song et al., "Regulation of IL-1beta-induced GM-CSF production in human airway smooth muscle cells by carbon monoxide," Am. J. Physiol. Lung Cell. Mol. Physiol., 284(1):L50-L56, (2003).

Stephens et al., "Further Observations Regarding Carbon Monoxide Gas as an Important Factor in the Causation of Industrial Cancer", *Medical Press and Circular* 183:283-288 (1933).

Stupfel and Bouley, "Physiological and Biochemical Effects on Rats and Mice Exposed to Small Concentrations of Carbon Monoxide for Long Periods," Ann. N.Y. Acad. Sci. 174:343-368 (1970).

Suganuma et al., "A new process of cancer prevention mediated through inhibition of tumor necrosis factor alpha expression," Cancer Res. 56(16):3711-5 (1996).

Tamayo et al., "Carbon monoxide inhibits hypoxic pulmonary vasoconstriction in rats by a cGMP-independent mechanism", *Pflugers Arch.* 434(6):698-704 (1997).

Taylor, "Anti-TNF Therapy for Rheumatoid Arthritis and Other Inflammatory Diseases", *Molecular Biotechnology* 19:153-168 (2001).

Tenderich et al., "Hemodynamic follow-up of cardiac allografts from poisoned donors," *Transplantation* 66(9):1163-7 (1998).

Tenhunen et al., "The Enzymatic Conversion of Heme to Bilirubin by Microsomal Heme Oxygenase," *Proc Natl Acad Sci* USA 61:748-755 (1968).

The Merck Manual (16th Ed. 1992) pp. 646-657.

The New Encyclopedia Britannica (15th ed. 1994) vol. 26, *Macropaedia*, p. 756.

Thom et al, "'Therapeutic' Carbon Monoxide May Be Toxic," Am. J. Respir. Crit. Care Med., 171(11):1318, (2005).

Tobiasch et al, "Heme oxygenase-1 protects pancreatic β cells from apoptosis caused by various stimuli," J. Investig. Med., 49:566-71, (2001).

Toda et al., "Exogenous carbon monoxide protects endothelial cells against oxidant stress and improves graft function after lung transplantation," Circulation, 98(17):1265 (1998).

Tulis et al., "Adenovirus-Mediated Heme Oxygenase-1 Gene Delivery Inhibits Injury-Induced Vascular Neointima Formation", *Circulation* 104:2710-2715 (2001).

Utz et al., "Carbon Monoxide Relaxes Heal Smooth Muscle Through Activation of Guanylate Cyclase," *Biochem Pharmacol.* 47:1195-201, 1991.

Vassalli et al., "Inhibition of Hypoxic Pulmonary Vasoconstriction By Carbon Monoxide in Dogs", European Respiratory Journal, ERS Annual Congress, Geneva, Switzerland, Sep. 19-23, 1998.

Verma et al., "Carbon Monoxide: a Putative Neural Messenger," *Science* 259:381-384, 1993.

Verran et al., "Use of Liver Allografts from Carbon Monoxide Poisoned Cadaveric Donors," *Transplantation* 62(10):1514-5 (1996).

Wang et al., "Carbon monoxide-induced vasorelaxation and the underlying mechanisms," Br. J. Pharmacol. 121:927-934 (1997).

Wang et al., "Resurgence of carbon monoxide: an endogenous gaseous vasorelaxing factor". *Can. J. Physiol. Pharmacol.* 76:1-15 (1998).

Weir et al., "Islet transplantation as a treatment for diabetes," *J. Am. Optom. Assoc.* 69:727-32, 2000.

Weir et al., "Scientific and Political Impediments to Successful Islet Transplantation," *Diabetes* 46:1247-56, 1997.

Welty et al., "Hyperoxic Lung Injury is Potentiated by SPC-Promotor Driven Expression of an HO-1 Transgene in Mice", *J Respiratory Critical Care Med* 159(3):A218 (1999).

Weng et al., "Transpulmonary HO-1 Gene Delivery in Neonatal Mice", *J Respiratory Critical Care Med* 159(3):A218 (1999).

Yamashita et al., "Effects of HO-1 induction and carbon monoxide on cardiac transplantation in mice," Exp. Biol. Med., 228(5):616, (2003), Abstract.

Yuan et al., "Evidence of increased endogenous carbon monoxide production in newborn rat endotoxicosis," *Chinese Medical Sciences Journal* (1997), vol. 12, No. 4, 212-215.

Zhang et al., "Carbon monoxide inhibition of apoptosis during ischemia-reperfusion lung injury is dependent on the p38 mitogen-activated protein kinase pathway and involves caspase 3," J. Biol. Chem., 278(2):1248-1258, (2003).

Zhang et al., "Mitogen-activated protein kinases regulate HO-1 gene transcription after ischemia-reperfusion lung injury," Am. J. Physiol. Lung Cell. Mol. Physiol., 283(4):L815-L829, (2002).

Zhou et al., "Endogenous carbon monoxide and acute lung injury," Section of Respiratory System Foreign Medical Sciences 19:185-187 (1999) (translation included).

Zuckerbraun and Billiar, "Heme oxygenase-1: a cellular Hercules" Hepatology, 37(4):742-744, (2003).

Zuckerbraun et al., "Carbon monoxide attenuated the development of necrotizing enterocolitis in an animal model," Surgical Infection Society 3:83 (2002).

Zuckerbraun et al., "Carbon monoxide inhibits intestinal inducible nitric oxide synthase production and ameliorates intestinal Inflammation in experimental NEC," J. Amer. College of Surgeons 197:S50 (2003).

Zuckerbraun et al., "Carbon Monoxide Protects Hepatocytes from TNF-alpha/Actinomycin D Induced Cell Death," Critical Care Medicine 29:A59 (2001).

\* cited by examiner

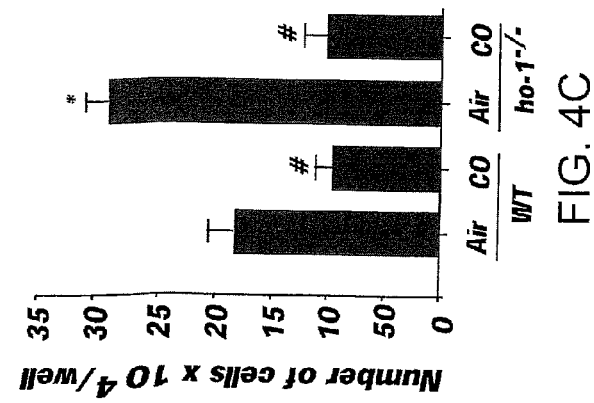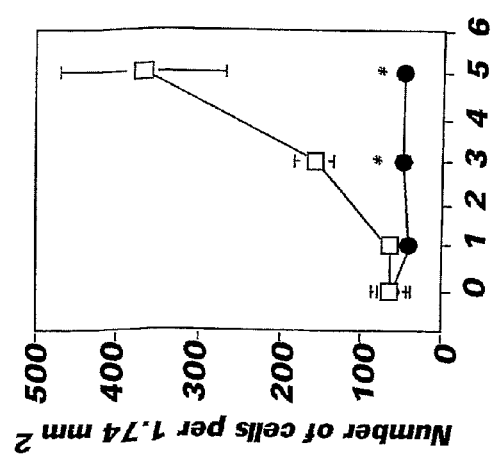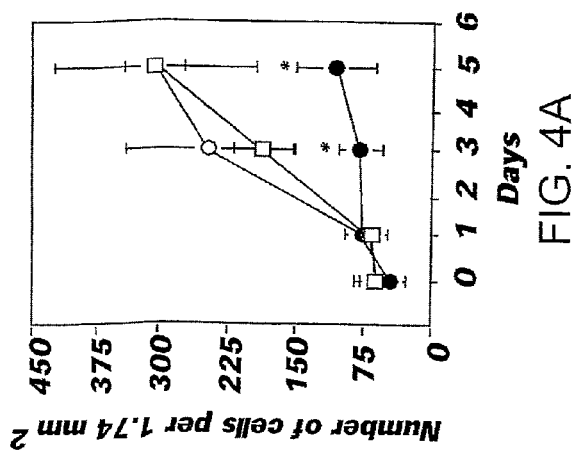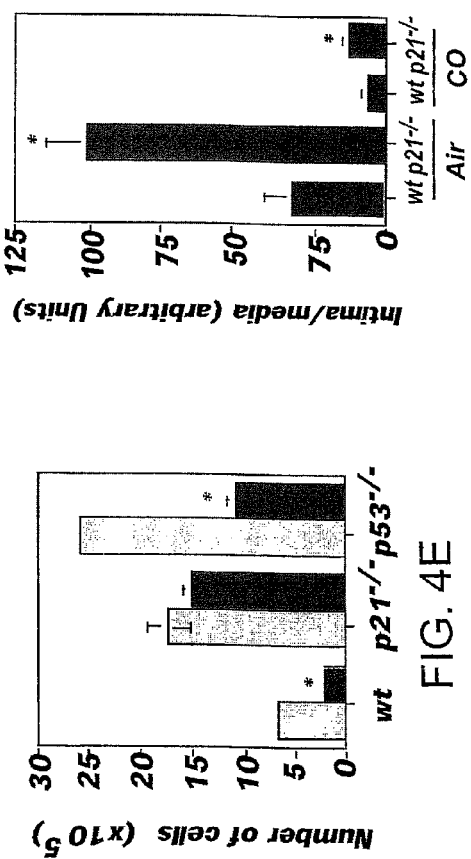

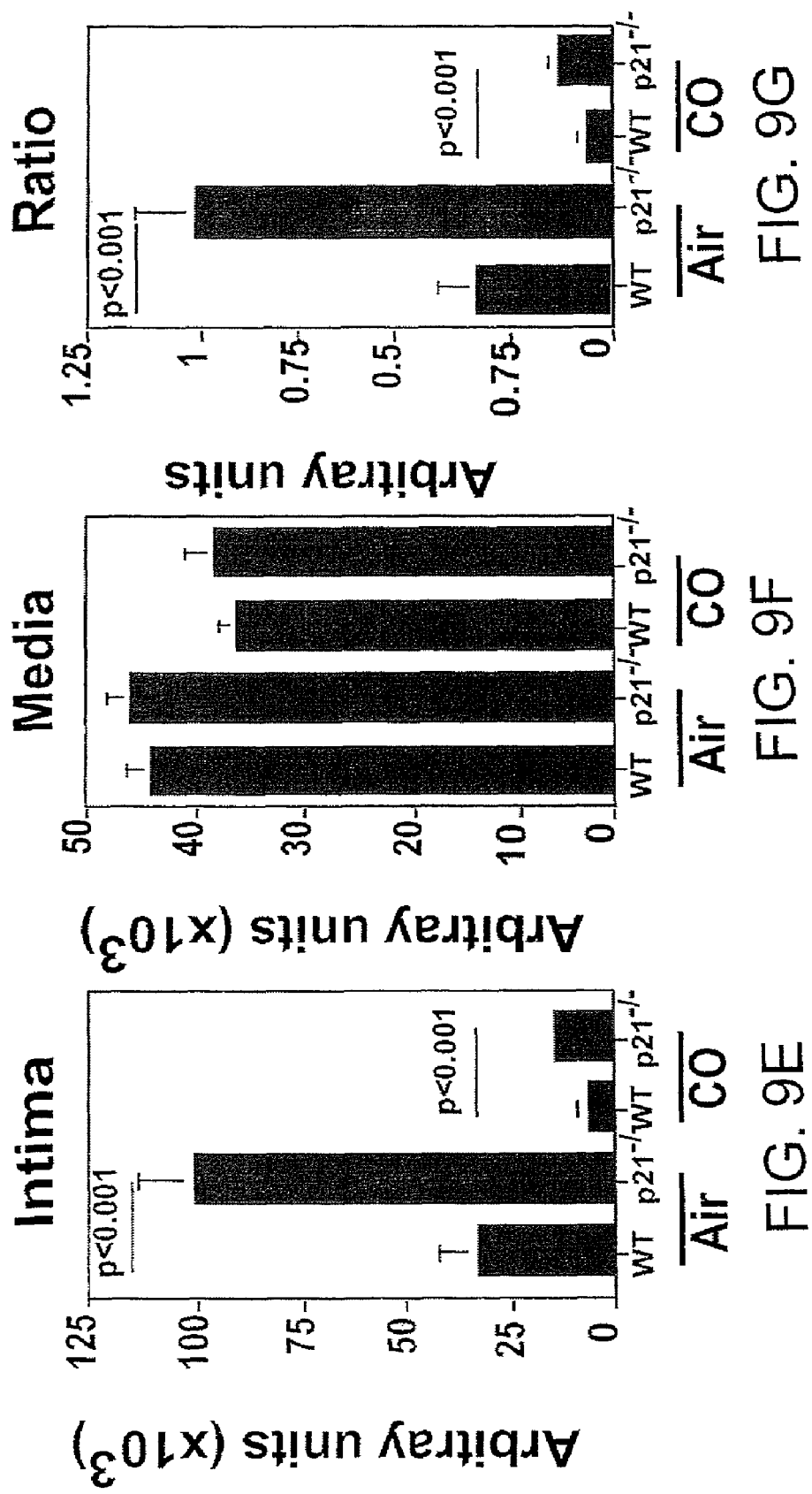

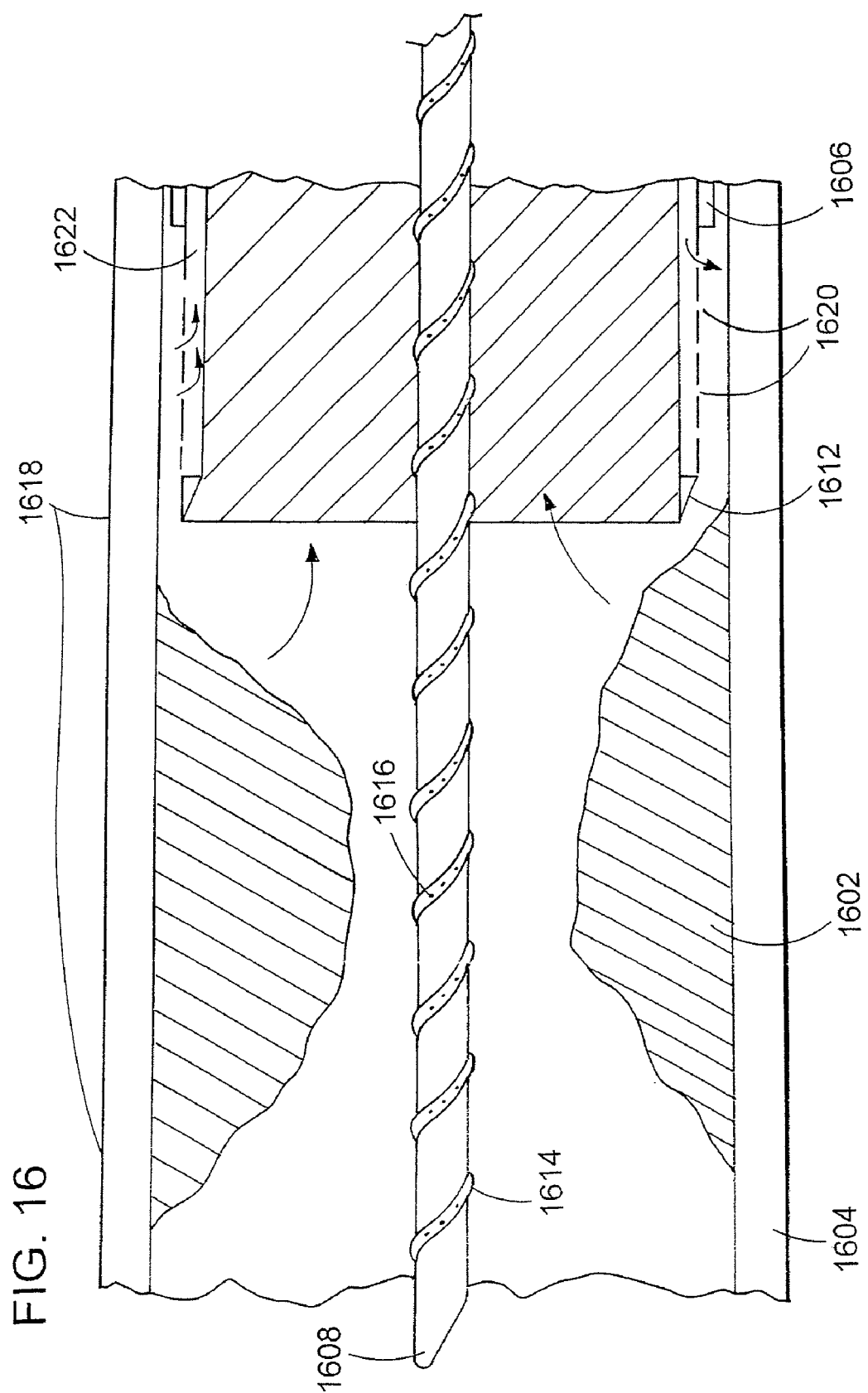

METHODS OF TREATING VASCULAR DISEASE

CROSS-REFERENCE TO RELATED APPLICATIONS

This application is a divisional of U.S. patent application Ser. No. 10/367,277, filed Feb. 13, 2003, which now U.S. Pat. No. 7,364,757, claims priority to U.S. Provisional Application No. 60/356,718 filed Feb. 13, 2002, both of which are incorporated herein by reference in their entirety.

STATEMENT AS TO FEDERALLY SPONSORED RESEARCH

This invention was made with Government support under National Institutes of Health Grant Nos. HL55330, HL60234, HL67040, HL58688, HL53458, HL60234, HL5785405, and AI42365. The Government has certain rights in this invention.

TECHNICAL FIELD

This invention generally relates to treating vascular disease.

BACKGROUND

Heme oxygenase-1 (HO-1) catalyzes the first step in the degradation of heme. HO-1 cleaves the α-meso carbon bridge of b-type heme molecules by oxidation to yield equimolar quantities of biliverdin IXa, carbon monoxide (CO), and free iron. Subsequently, biliverdin is converted to bilirubin via biliverdin reductase, and the free iron is sequestered into ferritin (the production of which is induced by the free iron).

CO is recognized as an important signaling molecule (Verma et al., Science 259:381-384, 1993). It has been suggested that carbon monoxide acts as a neuronal messenger molecule in the brain (Id.) and as a neuro-endocrine modulator in the hypothalamus (Pozzoli et al., Endocrinology 735: 2314-2317, 1994). Like nitric oxide, CO is a smooth muscle relaxant (Utz et al., Biochem Pharmacol. 47:195-201, 1991; Christodoulides et al., Circulation 97:2306-9, 1995) and inhibits platelet aggregation (Mansouri et al., Thromb Haemost. 48:286-8, 1982). Inhalation of low levels of CO has been shown to have anti-inflammatory effects in some models.

Intimal hyperplasia, a thickening of the inner layer of the blood vessel, is a pathological process that arises from vascular injury subsequent to procedures such as angioplasty, bypass surgery or organ transplantation. Intimal hyperplasia continues to limit the success of these therapeutic interventions.

SUMMARY

The present invention is based, in part, on the discoveries that CO prevents arteriosclerotic lesions and intimal hyperplasia following aortic transplant and carotid artery balloon injury in animals.

Accordingly, in one aspect, the invention provides a method of treating intimal hyperplasia in a patient. The method includes identifying a patient suffering from or at risk for intimal hyperplasia (e.g., intimal hyperplasia resulting from an angioplasty procedure or a transplant procedure, or resulting from a procedure or condition other than a transplant procedure), and administering to the patient a pharmaceutical composition comprising an amount of carbon monoxide effective to treat intimal hyperplasia in the patient.

The invention also provides a method of performing angioplasty in a patient. The method includes performing angioplasty in the patient, and before, during, and/or after performing angioplasty, administering to the patient a pharmaceutical composition comprising an amount of CO effective to treat intimal hyperplasia in the patient. The angioplasty can be any angioplasty procedure, e.g., balloon angioplasty; laser angioplasty; artherectomy, e.g., directional atherectomy, rotational atherectomy, or extraction atherectomy; and/or any angioplasty procedure using a stent, or any combination of such procedures.

The invention also provides a method of treating (e.g., preventing or decreasing) restenosis in a patient. The method includes providing a vessel containing a pressurized gas comprising carbon monoxide gas, identifying a patient suffering from or at risk for restenosis, releasing the pressurized gas from the vessel to form an atmosphere comprising carbon monoxide gas, and exposing the patient to the atmosphere, wherein the amount of carbon monoxide in the atmosphere is sufficient to treat restenosis in the patient.

In another aspect, the invention provides a method of treating restenosis in a patient. The method includes identifying a patient suffering from or at risk for restenosis and administering to the patient a pharmaceutical composition comprising an amount of carbon monoxide effective to treat restenosis in the patient. Restenosis can result from any angioplasty procedure, e.g., balloon angioplasty; laser angioplasty; artherectomy, e.g., directional atherectomy, rotational atherectomy, or extraction atherectomy; and/or any angioplasty procedure using a stent, or any combination of such procedures.

The invention also provides a method for performing vascular surgery, e.g., a transplant procedure, on a patient. The method includes: (a) performing vascular surgery (e.g., a transplant procedure) on a patient, and (b) before during and/or after (a), administering to the patient a pharmaceutical composition comprising an amount of CO effective to treat arteriosclerosis (e.g., intimal hyperplasia) in the patient.

In another aspect, the invention provides a method of inhibiting smooth muscle cell proliferation. The method includes providing a smooth muscle cell(s), and administering to the smooth muscle cell(s) an amount of CO effective to inhibit proliferation of the smooth muscle muscle cell(s). This can be carried out in vivo or in vitro.

A method of performing angioplasty in a patient is also provided, which includes providing an angioplasty device (e.g, a device described herein) capable of administering carbon monoxide to a patient, positioning the device in a blood vessel in need of angioplasty, performing angioplasty using the device, and before, during and/or after performing angioplasty, administering CO to the blood vessel using the device in an amount sufficient to treat intimal hyperplasia, to thereby perform angioplasty in the patient. The device can be any device capable of use in an angioplasty procedure, e.g., a device described herein. Alternatively or in addition, the device can be coated with a CO-releasing agent, e.g., a hydrogel, oil, or ointment, that releases CO or a CO-releasing compound.

In another aspect, the invention provides a vessel comprising medical grade compressed CO gas. The vessel can bear a label indicating that the gas can be used to reduce restenosis, arteriosclerosis, and/or intimal hyperplasia in a patient (e.g., a human patient), and/or that it can be used in an angioplasty procedure. The CO gas can be in an admixture with nitrogen gas, with nitric oxide and nitrogen gas, or with an oxygen-containing gas. The CO gas can be present in the admixture at a concentration of at least about 0.025%, e.g., at least about 0.05%, 0.10%, 0.50%, 1.0%, 2.0%, 10%, 50%, or 90%.

The invention also provides a kit that includes an angioplasty device (e.g., a balloon angioplasty device; a laser angioplasty device; an atherectomy device; and/or a stent) and a vessel containing CO (e.g., a liquid and/or gaseous CO composition). The angioplasty device is capable of administering carbon monoxide to a patient. The kit can further include instructions for use of the carbon monoxide composition in a method for performing angioplasty in a patient.

In another aspect, the invention provides angioplasty devices (e.g., balloon angioplasty devices, laser angioplasty devices, atherectomy devices, and stents, e.g., a device described herein) capable of administering CO to a patient and/or a blood vessel immediately before, during, and/or after an angioplasty procedure. In one embodiment, the angioplasty device comprises a CO composition. In another embodiment, the device is a balloon angioplasty device that includes an inflatable member (e.g., a balloon) having a plurality of apertures, and a reservoir containing CO (e.g., a liquid or gaseous CO composition) connected to the inflatable member, such that CO can be delivered from the reservoir through the inflatable member and to the blood vessel.

Also within the invention is the use of CO in the manufacture of a medicament for treatment or prevention of a condition described herein, e.g., intimal hyperplasia, restenosis, and/or arteriosclerosis. The medicament can also be used in a method for performing an angioplasty procedure and/or a transplantation procedure. The medicament can be in any form as described herein, e.g., a liquid or gaseous CO composition.

Unless otherwise defined, all technical and scientific terms used herein have the same meaning as commonly understood by one of ordinary skill in the art to which this invention belongs. Suitable methods and materials are described below, although methods and materials similar or equivalent to those described herein can be used in the practice or testing of the present invention. All publications, patent applications, patents, and other references mentioned herein are incorporated by reference in their entirety. In case of conflict, the present specification, including definitions, will control. The materials, methods, and examples are illustrative only and not intended to be limiting.

Other features and advantages of the invention will be apparent from the following detailed description, and from the claims.

BRIEF DESCRIPTION OF THE DRAWINGS

FIG. 4A is a line graph illustrating proliferation of rat SMC that were non-transduced (○; Medium), transduced with Lac.Z recombinant adenovirus (□; LacZ Rec. Ad.) or transduced with HO-1 recombinant adenovirus (●; HO-1 rec. Ad.).

FIG. 4B is a line graph illustrating proliferation of rat SMC in the presence (●; 1000 ppm) or absence (□) of CO.

FIG. 4C is a bar graph illustrating proliferation of SMC isolated from wild type (WT) or HO-1 deficient (ho-1$^{-/-}$) mice in the presence (CO) and absence (Air) of CO.

FIG. 4E is a bar graph illustrating the effect of CO on proliferation of mouse SMC isolated from wild type (wt), p21Cip1 (p21$^{-/-}$) and p53 (p53$^{-/-}$) deficient mice. Gray bars indicate cells exposed to room air and black bars cells exposed to CO (250 ppm).

FIG. 4F is a bar graph illustrating the intima/media area ratio of balloon-injured carotid arteries from wild type (C57/B16/S129; wt) and p21$^{-/-}$ mice exposed to air (Air) or carbon monoxide (CO).

FIG. 9E is a bar graph illustrating the mean relative areas (in arbitrary units) of the intima of wire-injured carotid arteries from wild type (wt) and p21$^{-/-}$ mice exposed to either air (Control) or 250 ppm CO (CO).

FIG. 9F is a bar graph illustrating the mean relative areas (in arbitrary units) of the media of wire-injured carotid arteries from wild type (wt) and p21$^{-/-}$ mice exposed to either air (Control) or 250 ppm CO (CO).

FIG. 9G is a bar graph illustrating the intima/media area ratio of wire-injured carotid arteries from wild type (wt) and p21$^{-/-}$ mice exposed to either air (Control) or 250 ppm CO (CO).

FIG. 16 illustrates an example of an atherectomy device capable of administering CO to a patient during an angioplasty procedure.

DETAILED DESCRIPTION

Figure 1A:
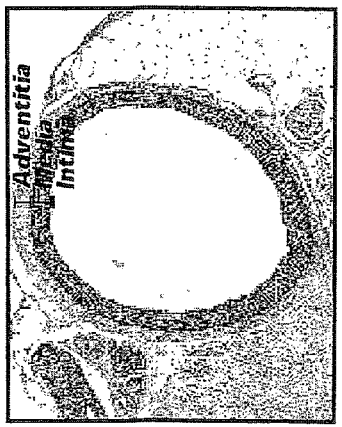
FIG. 1A is a photomicrograph (50× magnification) of a syngeneically transplanted aortic graft illustrating the effect of syngeneic transplantation on the graft.

The term "carbon monoxide" (or "CO") as used herein describes molecular carbon monoxide in its gaseous state, compressed into liquid form, or dissolved in aqueous solution. The term "carbon monoxide composition" or "pharmaceutical composition comprising carbon monoxide" is used throughout the specification to describe a gaseous or liquid composition containing carbon monoxide that can be administered to a patient and/or a blood vessel, e.g, a patient (or blood vessel) subjected to angioplasty, bypass surgery, transplant, or any other procedure that may/will result in intimal hyperplasia and/or arteriosclerosis. A skilled practitioner will recognize which form of the pharmaceutical composition, e.g., gaseous, liquid, or both gaseous and liquid forms, is preferred for a given application.

The term "intimal hyperplasia" is an art-recognized term and is used herein to refer to proliferation of cells, e.g., smooth muscle cells, within the intima of a blood vessel. The skilled practitioner will appreciate that intimal hyperplasia can be caused by any number of factors, e.g., mechanical, chemical and/or immunological damage to the intima. Intimal hyperplasia can often be observed in patients, for example, following balloon angioplasty or vascular surgery, e.g., vascular surgery involving vein grafts (e.g., transplant surgery). "Arteriosclerosis," "arteriosclerotic lesion," "arteriosclerotic plaque," and "arteriosclerotic condition" are also art recognized term terms, and are used herein to describe a thickening and hardening of the arterial wall. The term "vasculature" as used herein refers to the vascular system (or any part thereof) of a body, human or non-human, and includes blood vessels, e.g., arteries, arterioles, veins, venules, and capillaries. The term "restenosis" refers to re-narrowing of an artery following angioplasty.

The term "angioplasty" is an art-recognized term and refers to any procedure, singly or in combination, involving remodeling of a blood vessel, e.g., dilating a stenotic region in a patient's vasculature to restore adequate blood flow beyond the stenosis. Such procedures include percutaneous transluminal angioplasty (PTA), which employs a catheter having an expansible distal end, i.e., an inflatable balloon (known as "balloon angioplasty"); laser angioplasty; extraction atherectomy; directional atherectomy; rotational atherectomy; stenting; and any other procedure for remodeling a blood vessel, e.g., an artery.

The terms "effective amount" and "effective to treat," as used herein, refer to an amount or a concentration of carbon monoxide utilized for a period of time (including acute or chronic administration and periodic or continuous administration) that is effective within the context of its administration for causing an intended effect or physiological outcome. Effective amounts of carbon monoxide for use in the present invention include, for example, amounts that prevent or reduce intimal hyperplasia following a procedure, e.g., angioplasty. Effective amounts of carbon monoxide also include amounts that prevent or reduce arteriosclerosis in a patient, e.g., a transplant patient. The term "treat(ment)" is used herein to describe delaying the onset of, inhibiting, or alleviating the detrimental effects of a condition, e.g., intimal hyperplasia and/or arteriosclerosis.

For gases, effective amounts of CO generally fall within the range of about 0.0000001% to about 0.3% by weight, e.g., 0.0001% to about 0.25% by weight, preferably at least about 0.001%, e.g., at least about 0.005%, 0.010%, 0.02%, 0.025%, 0.03%, 0.04%, 0.05%, 0.06%, 0.08%, 0.10%, 0.15%, 0.20%, 0.22%, or 0.24% by weight of CO. Preferred ranges of CO include about 0.002% to about 0.24%, about 0.005% to about 0.22%, about 0.01% to about 0.20%, and about 0.02% to about 0.1% by weight. For liquid solutions of CO, effective amounts generally fall within the range of about 0.0001 to about 0.0044 g CO/100 g liquid, e.g., at least about 0.0001, 0.0002, 0.0004, 0.0006, 0.0008, 0.0010, 0.0013, 0.0014, 0.0015, 0.0016, 0.0018, 0.0020, 0.0021, 0.0022, 0.0024, 0.0026, 0.0028, 0.0030, 0.0032, 0.0035, 0.0037, 0.0040, or 0.0042 g CO/100 g aqueous solution. Preferred ranges include, e.g., about 0.0010 to about 0.0030 g CO/100 g liquid, about 0.0015 to about 0.0026 g CO/100 g liquid, or about 0.0018 to about 0.0024 g CO/100 g liquid. A skilled practitioner will appreciate that amounts outside of these ranges may be used depending upon the application.

The term "patient" is used throughout the specification to describe an animal, human or non-human, to whom treatment according to the methods of the present invention is provided. Veterinary and non-veterinary applications are contemplated by the present invention. The term includes but is not limited to mammals, e.g., humans, other primates, pigs, rodents such as mice and rats, rabbits, guinea pigs, hamsters, cows, horses, cats, dogs, sheep and goats.

The term "transplantation" is used throughout the specification as a general term to describe the process of transferring an organ or tissue into a patient. The term "transplantation" is defined in the art as the transfer of living tissues or cells from a donor to a recipient, with the intention of maintaining the functional integrity of the transplanted tissue or cells in the recipient (see, e.g., *The Merck Manual*, Berkow, Fletcher, and Beers, Eds., Merck Research Laboratories, Rahway, N.J., 1992). The term includes all categories of transplants known in the art. Transplants are categorized by site and genetic relationship between donor and recipient. The term includes, e.g., autotransplantation (removal and transfer of cells or tissue from one location on a patient to the same or another location on the same patient), allotransplantation (transplantation between members of the same species), and xenotransplantation (transplantations between members of different species).

The term "donor" or "donor patient" as used herein refers to an animal (human or non-human) from whom an organ or tissue can be obtained for the purposes of transplantation to a recipient patient. The term "recipient" or "recipient patient" refers to an animal (human or non-human) into which an organ or tissue can be transferred.

The terms "organ rejection", "transplant rejection" and "rejection" are art-recognized and are used throughout the specification as general terms to describe the process of rejection of an organ, tissues, or cells in a recipient. Included within the definition are, for example, three main patterns of rejection that are typically identified in clinical practice: hyperacute rejection, acute rejection, and chronic rejection (see, e.g., *Oxford Textbook of Surgery*, Morris and Malt, Eds., Oxford University Press (1994)).

The term "organ(s)" is used throughout the specification as a general term to describe any anatomical part or member having a specific function in the animal. Further included within the meaning of this term are substantial portions of organs, e.g., cohesive tissues obtained from an organ. Such organs include but are not limited to kidney, liver, heart, intestine, e.g., large or small intestine, pancreas, and lungs. Also included in this definition is vasculature, e.g., veins and arteries, and bones.

Individuals considered at risk for developing intimal hyperplasia or arteriosclerosis may benefit particularly from the invention, primarily because prophylactic CO treatment can be administered before a procedure is performed on a patient or before there is any evidence of intimal hyperplasia or an arteriosclerotic plaque. Individuals "at risk" include, e.g., patients that have or will have any type of mechanical, chemical and/or immunological damage to the intima, e.g., patients that will or have undergone transplant surgery and/or angioplasty. Skilled practitioners will appreciate that a patient can be determined to be at risk for intimal hyperplasia or arteriosclerosis by any method known in the art, e.g., by a physician's diagnosis.

Preparation of Gaseous Compositions

A CO composition may be a gaseous composition. Compressed or pressurized gas useful in the methods of the invention can be obtained from any commercial source, and in any type of vessel appropriate for storing compressed gas. For example, compressed or pressurized gases can be obtained from any source that supplies compressed gases, such as oxygen, for medical use. The term "medical grade" gas, as used herein, refers to gas suitable for administration to patients as defined herein. The pressurized gas including CO used in the methods of the present invention can be provided such that all gases of the desired final composition (e.g., CO, He, NO, $CO_2$, $O_2$, $N_2$) are in the same vessel, except that NO and $O_2$ cannot be stored together. Optionally, the methods of the present invention can be performed using multiple vessels containing individual gases. For example, a single vessel can be provided that contains carbon monoxide, with or without other gases, the contents of which can be optionally mixed with the contents of other vessels, e.g., vessels containing oxygen, nitrogen, carbon dioxide, compressed air, or any other suitable gas or mixtures thereof.

Gaseous compositions administered to a patient according to the present invention typically contain 0% to about 79% by weight nitrogen, about 21% to about 100% by weight oxygen and about 0.0000001% to about 0.3% by weight (corresponding to about 1 ppb or 0.001 ppm to about 3,000 ppm) CO. Preferably, the amount of nitrogen in the gaseous composition is about 79% by weight, the amount of oxygen is about 21% by weight and the amount of CO is about 0.0001% to about 0.25% by weight. The amount of CO is preferably at least about 0.001%, e.g., at least about 0.005%, 0.01%, 0.02%, 0.025%, 0.03%, 0.04%, 0.05%, 0.06%, 0.08%, 0.10%, 0.15%, 0.20%, 0.22%, or 0.24% by weight. Preferred ranges of CO include 0.005% to about 0.24%, about 0.01% to about 0.22%, about 0.015% to about 0.20%, and about 0.025% to about 0.1% by weight. It is noted that gaseous CO compositions having concentrations of CO greater than 0.3% (such as 1% or greater) may be used for short periods (e.g., one or a few breaths), depending upon the application.

A gaseous CO composition may be used to create an atmosphere that comprises CO gas. An atmosphere that includes appropriate levels of CO gas can be created, for example, by providing a vessel containing a pressurized gas comprising CO gas, and releasing the pressurized gas from the vessel into a chamber or space to form an atmosphere that includes the CO gas inside the chamber or space. Alternatively, the gases can be released into an apparatus that culminates in a breathing mask or breathing tube, thereby creating an atmosphere comprising CO gas in the breathing mask or breathing tube, ensuring the patient is the only person in the room exposed to significant levels of CO.

CO levels in an atmosphere can be measured or monitored using any method known in the art. Such methods include electrochemical detection, gas chromatography, radioisotope counting, infrared absorption, colorimetry, and electrochemical methods based on selective membranes (see, e.g., Sunderman et al., Clin. Chem. 28:2026-2032, 1982; Ingi et al., Neuron 16:835-842, 1996). Sub-parts per million CO levels can be detected by, e.g., gas chromatography and radioisotope counting. Further, it is known in the art that CO levels in the sub-ppm range can be measured in biological tissue by a midinfrared gas sensor (see, e.g., Morimoto et al., Am. J. Physiol. Heart. Circ. Physiol 280:H482-H488, 2001). CO sensors and gas detection devices are widely available from many commercial sources.

Preparation of Liquid Compositions

A pharmaceutical composition comprising CO may also be a liquid composition. A liquid can be made into a pharmaceutical composition comprising CO by any method known in the art for causing gases to become dissolved in liquids. For example, the liquid can be placed in a so-called "$CO_2$ incubator" and exposed to a continuous flow of CO, preferably balanced with carbon dioxide, until a desired concentration of CO is reached in the liquid. As another example, CO gas can be "bubbled" directly into the liquid until the desired concentration of CO in the liquid is reached. The amount of CO that can be dissolved in a given aqueous solution increases with decreasing temperature. As still another example, an appropriate liquid may be passed through tubing that allows gas diffusion, where the tubing runs through an atmosphere comprising CO (e.g., utilizing a device such as an extracorporeal membrane oxygenator). The CO diffuses into the liquid to create a liquid CO composition.

It is likely that such a liquid composition intended to be introduced into a living animal will be at or about 37° C. at the time it is introduced into the animal.

The liquid can be any liquid known to those of skill in the art to be suitable for administration to patients (see, for example, Oxford Textbook of Surgery, Morris and Malt, Eds., Oxford University Press (1994)). In general, the liquid will be an aqueous solution. Examples of solutions include Phosphate Buffered Saline (PBS), Celsior™, Perfadex™, Collins solution, citrate solution, and University of Wisconsin (UW) solution (Oxford Textbook of Surgery, Morris and Malt, Eds., Oxford University Press (1994)). In one embodiment of the present invention, the liquid is Ringer's Solution, e.g., lactated Ringer's Solution, or any other liquid that can be used infused into a patient. In another embodiment, the liquid includes blood, e.g., whole blood.

Any suitable liquid can be saturated to a set concentration of CO via gas diffusers. Alternatively, pre-made solutions that have been quality controlled to contain set levels of CO can be used. Accurate control of dose can be achieved via measurements with a gas permeable, liquid impermeable membrane connected to a CO analyzer. Solutions can be saturated to desired effective concentrations and maintained at these levels.

Treatment of Patients and Vasculature with CO Compositions

The present invention contemplates administering CO compositions to patients and/or portions of their vasculature before, during, and/or after the patient undergoes angioplasty, transplant surgery, vascular surgery, or any other procedure that causes/increases the risk of intimal hyperplasia, restenosis, and/or arteriosclerosis in the patient. A patient can be treated systemically with gaseous and/or liquid CO compositions by any method known in the art for administering gases and/or liquids to patients, e.g., by inhalation of the gas and intravenous or intraarterial administration of the liquid. With systemic treatment, substantially all of the patient's vasculature can be treated with CO. A portion of a patient's vasculature, e.g., a specific vein or artery, can be treated by administering a gaseous or liquid CO composition directly to the vein or artery. Although the present invention is not limited to any particular mode for administering CO compositions to patients and/or portions of their vasculature, various treatments are discussed in detail below.

Systemic Delivery of Gaseous CO

Gaseous CO compositions can be delivered systemically to a patient, e.g., a patient suffering from or at risk for intimal hyperplasia (e.g., restenosis and/or arteriosclerosis). Gaseous CO compositions are typically administered by inhalation through the mouth or nasal passages to the lungs, where the CO is readily absorbed into the patient's bloodstream. The concentration of active compound (CO) utilized in the therapeutic gaseous composition will depend on absorption, distribution, inactivation, and excretion (generally, through respiration) rates of the CO as well as other factors known to those of skill in the art. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. Acute, sub-acute and chronic administration of CO are contemplated by the present invention. CO can be delivered to the patient for a time (including indefinitely) sufficient to treat the condition and exert the intended pharmacological or biological effect.

The following are examples of some methods and devices that can be utilized to administer gaseous CO compositions to patients.

Ventilators

Medical grade CO (concentrations can vary) can be purchased mixed with air or another oxygen-containing gas in a standard tank of compressed gas (e.g., 21% $O_2$, 79% $N_2$). It is non-reactive, and the concentrations that are required for the methods of the present invention are well below the combustible range (10% in air). In a hospital setting, the gas presumably will be delivered to the bedside where it will be mixed with oxygen or house air in a blender to a desired concentration in ppm (parts per million). The patient will inhale the gas mixture through a ventilator, which will be set to a flow rate based on patient comfort and needs. This is determined by pulmonary graphics (i.e., respiratory rate, tidal volumes etc.). Fail-safe mechanism(s) to prevent the patient from unnecessarily receiving greater than desired amounts of carbon monoxide can be designed into the delivery system. The patient's CO level can be monitored by studying (1) carboxyhemoglobin (COHb), which can be measured in venous blood, and (2) exhaled CO collected from a side port of the ventilator. CO exposure can be adjusted based upon the patient's health status and on the basis of the markers. If necessary, CO can be washed out of the patient by switching to 100% $O_2$ inhalation. CO is not metabolized; thus, whatever is inhaled will ultimately be exhaled except for a very small percentage that is converted to $CO_2$. CO can also be mixed with any level of $O_2$ to provide therapeutic delivery of CO without consequential hypoxic conditions.

Face Mask and Tent

A CO-containing gas mixture is prepared as above to allow passive inhalation by the patient using a facemask or tent. The concentration inhaled can be changed and can be washed out by simply switching over to 100% $O_2$. Monitoring of CO levels would occur at or near the mask or tent with a fail-safe mechanism that would prevent too high of a concentration of CO from being inhaled.

Portable Inhaler

Compressed CO can be packaged into a portable inhaler device and inhaled in a metered dose, for example, to permit intermittent treatment of a recipient who is not in a hospital setting. Different concentrations of CO could be packaged in the containers. The device could be as simple as a small tank (e.g., under 5 kg) of appropriately diluted CO with an on-off valve and a tube from which the patient takes a whiff of CO according to a standard regimen or as needed.

Intravenous Artificial Lung

An artificial lung (a catheter device for gas exchange in the blood) designed for $O_2$ delivery and $CO_2$ removal can be used for CO delivery. The catheter, when implanted, resides in one of the large veins and would be able to deliver CO at desired concentrations either for systemic delivery or at a local site. The delivery can be a local delivery of a high concentration of CO for a short period of time at the site of an angioplastic procedure (this high concentration would rapidly be diluted out in the bloodstream), or a relatively longer exposure to a lower concentration of CO. Examples of an artificial lungs are described, e.g., in Hattler et al., Artif. Organs 18(11):806-812 (1994); and Golob et al., ASAIO J., 47(5):432-437 (2001). As used herein, the term "intravessel carbon monoxide delivery device" refers to a catheter device, e.g., an artificial lung (or modified version thereof) capable of residing in a blood vessel for extended periods of time (including indefinitely) and delivering CO to the patient systemically and/or locally.

Normobaric Chamber

In certain instances, it would be desirable to expose the whole patient to CO. The patient would be inside an airtight chamber that would be flooded with CO at a level that does not endanger the patient, or at a level that poses an acceptable risk without the risk of bystanders' being exposed. Upon completion of the exposure, the chamber could be flushed with air (e.g., 21% $O_2$, 79% $N_2$) and samples could be analyzed by CO analyzers to ensure no CO remains before allowing the patient to exit the exposure system.

Systemic Delivery of Liquid CO Compositions

The present invention further contemplates that liquid CO compositions can be created for systemic delivery to a patient, e.g., by intravenous or intraarterial infusion into a patient. For example, liquid CO compositions, such as CO-saturated Ringer's Solution, can be infused into a patient before, during, and/or after an angioplastic or transplant procedure. Alternatively or in addition, CO-partially or completely saturated whole (or partial) blood can be infused into the patient. The present invention also contemplates that agents capable of delivering doses of CO gas or liquids can be utilized (e.g., CO releasing gums, creams, ointments or patches).

Delivery of CO to Portions of the Vasculature

In Situ Treatment

Alternatively or in addition to systemic treatment, carbon monoxide compositions can be applied directly to any portion of a patient's vasculature that has or is at risk for intimal hyperplasia and/or arteriosclerosis. A gaseous composition can be applied directly to a portion of a patient's vasculature, e.g., to an affected artery, by any method known in the art for administering gases into a patient's vasculature. For example, CO can be delivered to an artery before, during, and/or after an angioplastic (e.g., balloon angioplasty) or surgical (e.g., transplant) procedure through a device similar to the intravenous artificial lung described above. As another example, any device used for performing an angioplastic procedure can be modified to administer CO to a patient's vasculature through the instrument while angioplasty is being performed. Such devices are discussed in further detail below.

Liquid CO compositions can also be applied directly to a portion of a patient's vasculature. Liquid CO compositions can be administered by any method known in the art for administering liquids to the vasculature of a patient. For example, a liquid CO composition can be administered to a specific vein (e.g., by intravenous injection) or artery (e.g., by intraarterial injection) before, during, and/or after a procedure. As another example, as described above, any instrument used in angioplastic procedures can be modified to administer to a vein or artery a liquid CO composition while an angioplastic procedure is being performed.

Ex Vivo Treatment

The present invention further contemplates use of CO compositions to prevent or reduce intimal hyperplasia and/or arteriosclerosis in transplanted vasculature, e.g., individual blood vessels (e.g., vein or aortic transplants) or blood vessels that remain associated with a transplantable organ (e.g., kidney, liver, heart, or lung). Alternative or in addition to the in situ exposures described above, exposure of vasculature to CO compositions can occur ex vivo. For example, prior to transplanting individual blood vessels or an organ with its associated vasculature into a recipient patient, the vasculature may be exposed to an atmosphere comprising carbon monoxide gas, to a liquid carbon monoxide composition, e.g., a liquid perfusate, storage solution, or wash solution having carbon monoxide dissolved therein, or both.

Exposure of vasculature to gaseous CO compositions ex vivo can be performed in any chamber or area suitable for creating an atmosphere that includes appropriate levels of CO gas. Such chambers include, for example, incubators and chambers built for the purpose of accommodating an organ in a preservation solution. As another example, an appropriate chamber may be a chamber wherein only the gases fed into the chamber are present in the internal atmosphere, such that the concentration of carbon monoxide can be established and maintained at a given concentration and purity, e.g., where the chamber is airtight. For example, a $CO_2$ incubator may be used to expose vasculature to a carbon monoxide composition, wherein carbon monoxide gas is supplied in a continuous flow from a vessel that contains the gas.

Exposure of vasculature to liquid CO compositions ex vivo may be performed in any chamber or space having sufficient volume for submerging the vasculature, completely or partially, in a liquid CO composition. Vasculature can also be exposed to such compositions by placing the vasculature in any suitable container, and causing a liquid CO composition to "wash over" or through the vasculature, such that the vasculature is exposed to a continuous flow of the CO composition. As yet another example, the vasculature may be submerged in a medium or solution that does not include CO, and placed in a chamber such that the medium or solution can be made into a CO composition via exposure to a CO-containing atmosphere as described herein. As still another example, the vasculature may be submerged in a liquid that does not include CO, and CO can be "bubbled" into the liquid.

Devices

The present invention contemplates administering CO to a patient's vasculature using a device that is capable of being used for both performing an angioplasty procedure and administering CO to a patient's vasculature. CO can be administered through and/or by the instrument, or by a CO-delivering coating thereon, while angioplasty is being performed (e.g., immediately before, during, and/or immediately after angioplasty is performed). Such devices include devices used for balloon angioplasty ("balloon angioplasty devices"), laser angioplasty ("laser angioplasty devices"), and devices used for atherectomy ("atherectomy devices"), e.g., extraction atherectomy; directional atherectomy; rotational atherectomy; and stents. As used herein, an "angioplasty device" is any device that can be used to perform angioplasty on a patient.

Figure 13A:
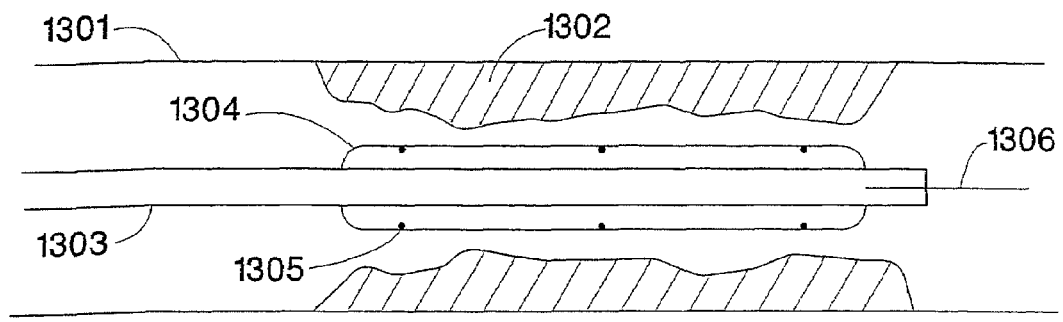
FIGS. 13A-13B illustrate an example of balloon angioplasty device capable of administering CO to a patient during an angioplasty procedure, at various stages of operation.

Referring to FIGS. 13A to 13D, examples of a catheter device with an inflatable member (e.g., a balloon) designed to administer CO (e.g., a liquid or gaseous CO composition) to a patient during angioplasty are shown. In FIG. 13A, the catheter 1303 is shown in position within a stenotic region 1302 of blood vessel 1301. The inflatable member 1304 is shown in the deflated state. The inflatable member includes at least one aperture 1305, through which CO can be administered to the vessel during the procedure. CO can be provided to the inflatable member (e.g., to inflate the inflatable member) from a reservoir (not shown) containing CO, e.g., a pharmaceutical composition comprising carbon monoxide. The device can optionally be guided to the intended site by a guide wire 1306.

Figure 13B:
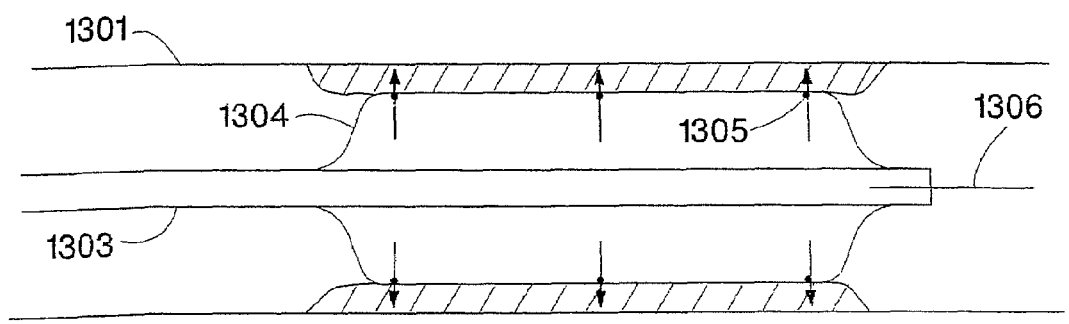

In FIG. 13B, the catheter 1303 is shown with the inflatable member 1304 in an inflated state. CO can be administered through the aperture(s) 1305 to the vessel 1301. In one embodiment, the inflatable member is inflated with CO, or a mixture of gases including CO, such that an amount of the CO sufficient to treat intimal hyperplasia flows out of the aperture(s) 1305 and is delivered to the blood vessel 1301 during and/or after inflation of the inflatable member 1304.

Figure 13C:
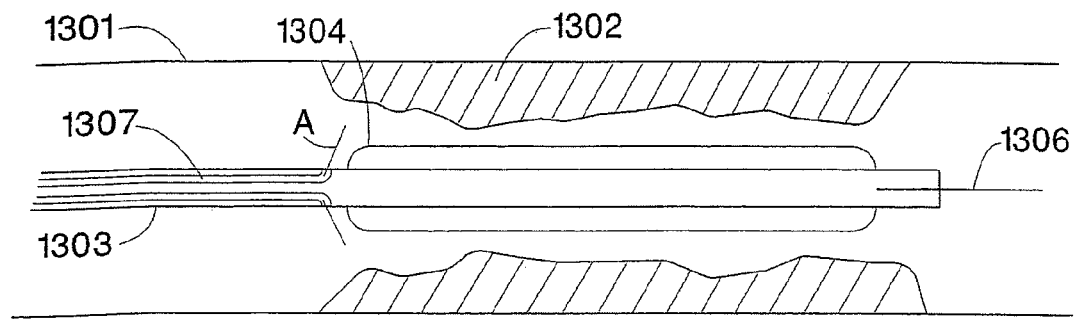
FIGS. 13C-13D illustrate alternative embodiments of the balloon angioplasty device.
Figure 13D:
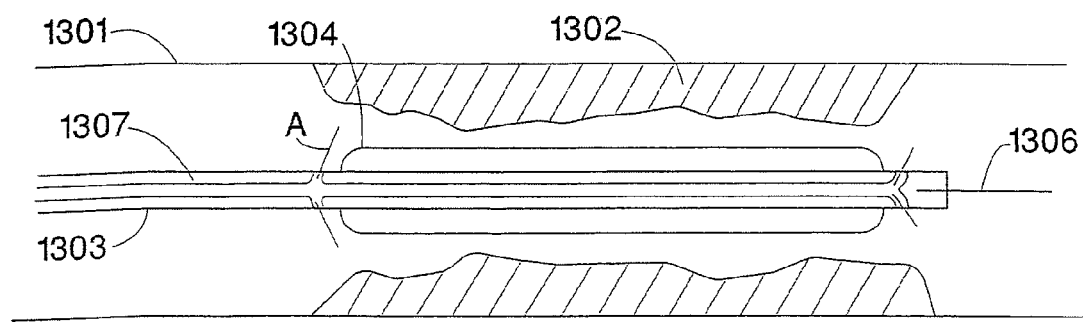

FIG. 13C illustrates another embodiment of the catheter device, wherein the catheter 1303 includes at least one lumen 1307 for delivering CO to the blood vessel 1301 during the angioplasty procedure. Still another embodiment is shown in FIG. 13D, wherein a central lumin 1307 delivers CO to a plurality of sites in the blood vessel 1301. A reservoir containing CO (not shown) can be connected to the lumin 1307, such that a dose of CO is administered from the reservoir through the lumin 1307 to the blood vessel.

Alternatively or in addition, the inflatable member 1304 can be coated with a CO-releasing coating, e.g., a hydrogel containing a CO composition, such that CO is delivered to the stenotic region 1302, e.g., upon contact with the inflatable member 1304.

Figure 14A:
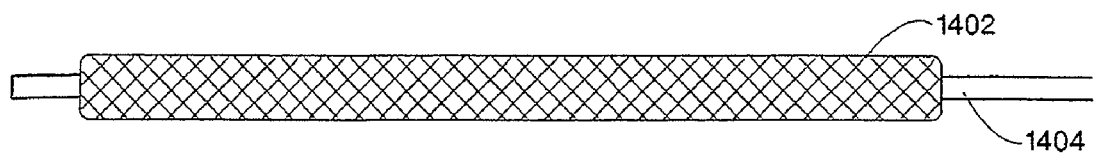
FIGS. 14A-14B illustrate an example of a stent capable of administering CO to a patient during an angioplasty procedure, at various stages of operation.
Figure 14B:
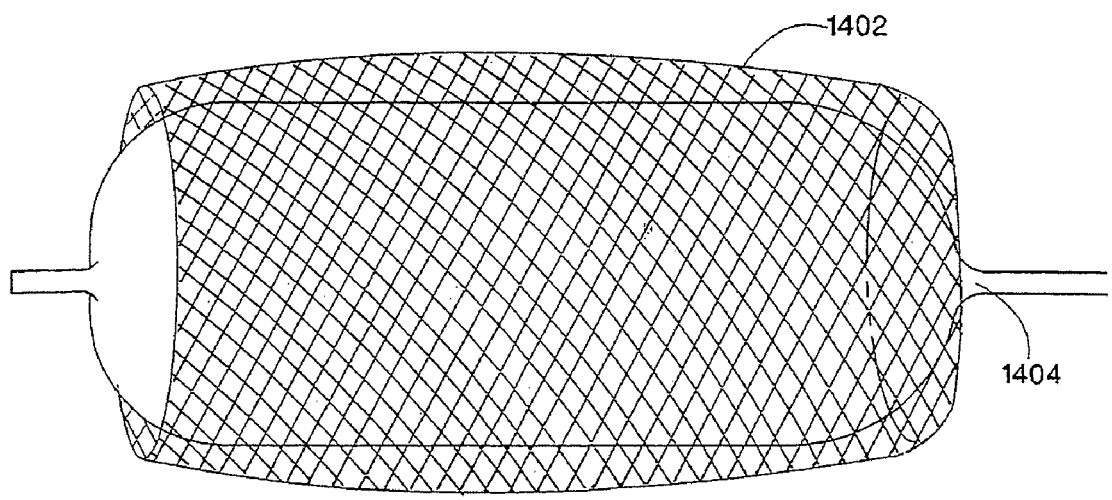

Referring to FIGS. 14A to 14B, an example of a stent designed to administer CO to a patient is shown. The term "stent" is an art-recognized term and refers to a mesh tube, typically made of wire, used to maintain a blood vessel in an open position, e.g., a blood vessel that has recently been remodeled during angioplasty. In FIG. 14A, a stent 1402 is shown in a collapsed state. The stent covers a balloon catheter 1404, shown in FIG. 14A in a deflated state. In FIG. 14B, the stent 1402 and balloon catheter 1404 are shown in an expanded/inflated state. Upon inflation of the balloon catheter 1404, the stent 1402 expands, locks in place, and forms a scaffold as shown in FIG. 14B, thereby holding the blood vessel in an open position. In one embodiment of the present invention, the stent 1402 is coated with a CO-releasing coating, e.g., a hydrogel that releases CO, such that an amount of CO sufficient to treat intimal hyperplasia is delivered to the blood vessel for an appropriate amount of time, e.g., for as long as the stent remains in place.

Figure 15:
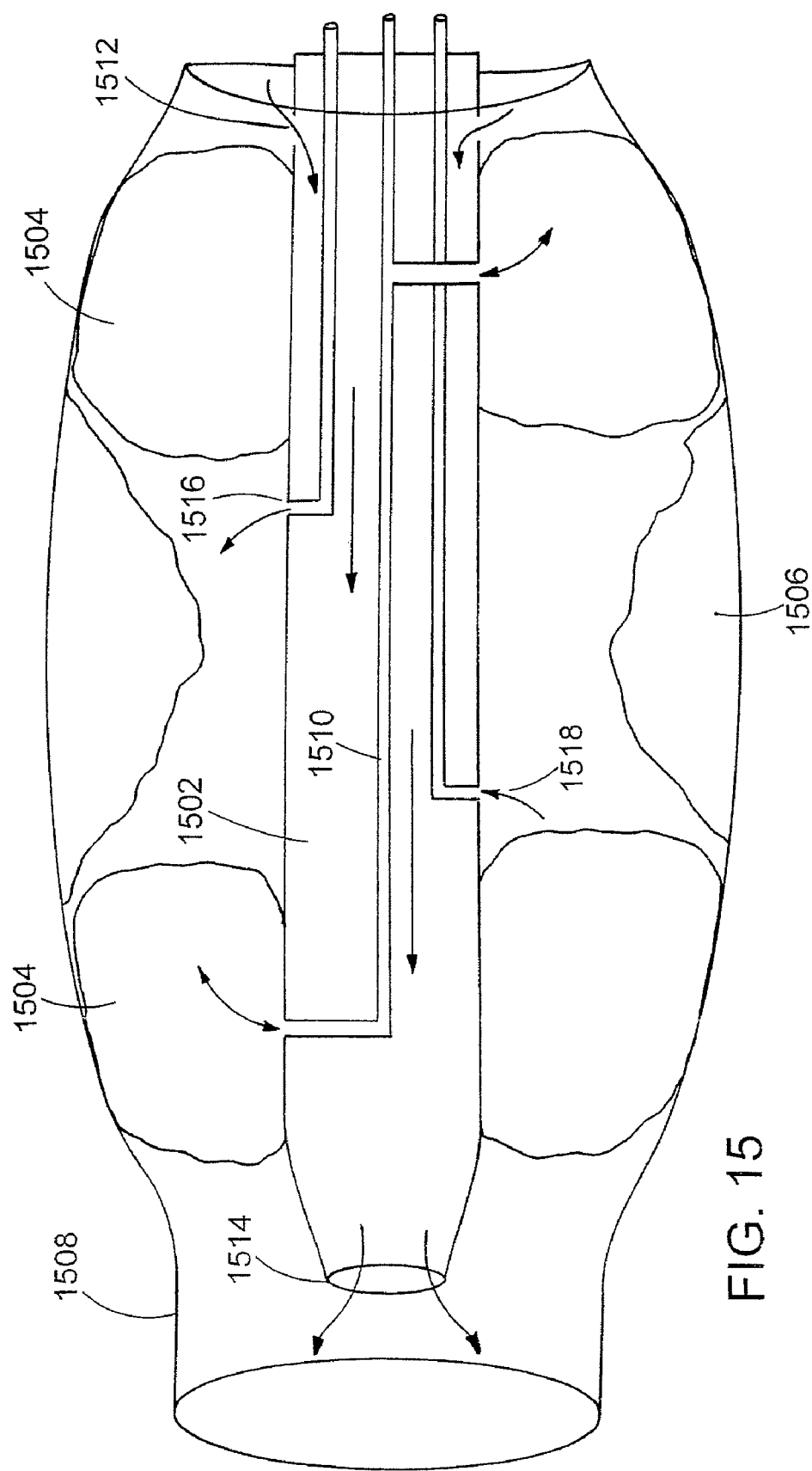
FIG. 15 illustrates an example of balloon angioplasty device with multiple balloons designed to administer CO to a patient during an angioplasty procedure.

Referring to FIG. 15, a catheter 1502 with two inflatable members 1504 is shown. The inflatable members 1504 can be used to isolate a stenotic region 1506, such that CO can be administered to the stenotic region 1506 between the inflatable members 1504. The catheter 1502 is inserted into the blood vessel 1508 prior to inflation of the inflatable members 1504. The inflatable members 1504 are then inflated using an inflation/deflation tube 1510 housed within the catheter 1502. The inflatable members 1504 in their inflated state obstruct the flow of blood to the region of the blood vessel undergoing treatment. Intake ducts 1512 on the proximal end of the catheter allow blood to flow into and through the catheter 1502 to outlet ducts 1514 located on the distal end of the catheter. This allows the blood to continue flowing to the rest of the artery 1508 while the local site of the artery 1506 is treated. CO can be introduced to the isolated region through an administering supply tube 1516. The inflated inflatable members 1504 provide an isolated treatment area within which appropriate levels of CO can be administered to the vessel. In addition, fiber probes (not shown) can be secured to the casing of the catheter 1502, and the site can be exposed to electromagnetic radiation through the fiber probes. CO can be administered to the site before, during, and/or after treatment of the site with electromagnetic radiation.

Referring to FIG. 16, an example of an instrument capable of administering CO to a patient while performing atherectomy is shown. Atherectomy involves cutting away and removing plaque 1602 from blood vessel walls 1604. The catheter 1606 is positioned within the artery 1604. A flexible guide 1608 is used to move the instrument through the region of treatment 1610. Rotating cutting blades 1612 are then extended beyond the catheter 1606. The rotating cutting blades 1612 follow the flexible guide 1608 and cut through the plaque 1602. The rotating cutting blades 1612 draw the removed particles of plaque into and towards the proximal end of the catheter 1606. CO can be introduced to the treated region through an administering tube 1614 within the catheter 1606. An administering tube 1614 can be secured to the guide 1608. CO can be administered through the catheter 1606 through a least one pore 1616 on the distal end of the administering tube 1614. Alternatively or in addition to supplying CO through an administering tube 1614, ducts 1620 and 1622 can be housed within the walls of the cutting blades 1612. Carbon monoxide can be supplied through an outlet duct 1620. At the conclusion of treatment an inlet duct 1622 can remove the CO. CO can be administered before, during, and/or after removal of plaques.

In addition to the above, a skilled practitioner will appreciate that any device known in the art for performing angioplasty procedures can be modified to administer CO to a patient's vasculature during use. Examples of such devices can be found, e.g., in U.S. Pat. Nos. 6,409,716, 5,985,307, 6,508,787, 5,709,875 and 6,450,989. Further, a skilled practitioner will recognize that any such devices can be coated with a CO-delivering agent, e.g., an oil, ointment or hydrogel, capable of releasing effective doses of CO, such that the CO is delivered to blood vessel upon contact with the instrument/ coating.

Use of Hemoxygenase-1 and Other Compounds

Also contemplated by the present invention is the induction or expression of hemeoxygenase-1 (HO-1) in conjunction with administration of carbon monoxide. HO-1 can be provided to a patient by inducing or expressing HO-1 in the patient, or by administering exogenous HO-1 directly to the patient. As used herein, the term "induce(d)" means to cause increased production of a protein, e.g., HO-1, in isolated cells or the cells of a tissue, organ or animal using the cells' own endogenous (e.g., non-recombinant) gene that encodes the protein.

HO-1 can be induced in a patient by any method known in the art. For example, production of HO-1 can be induced by hemin, by iron protoporphyrin, or by cobalt protoporphyrin. A variety of non-heme agents including heavy metals, cytokines, hormones, nitric oxide, $COCl_2$, endotoxin and heat shock are also strong inducers of HO-1 expression (Otterbein et al., Am. J. Physiol. Lung Cell Mol. Physiol. 279:L1029-L1037, 2000; Choi et al., Am. J. Respir. Cell Mol. Biol. 15:9-19, 1996; Maines, Annu. Rev. Pharmacol. Toxicol. 37:517-554, 1997; and Tenhunen et al., J. Lab. Clin. Med. 75:410-421, 1970). HO-1 is also highly induced by a variety of agents and conditions that create oxidative stress, including hydrogen peroxide, glutathione depletors, UV irradiation and hyperoxia (Choi et al., Am. J. Respir. Cell Mol. Biol. 15: 9-19, 1996; Maines, Annu. Rev. Pharmacol. Toxicol. 37:517-554, 1997; and Keyse et al., Proc. Natl. Acad. Sci. USA 86:99-103, 1989). A "pharmaceutical composition comprising an inducer of HO-1" means a pharmaceutical composition containing any agent capable of inducing HO-1 in a patient, e.g., any of the agents described above, e.g., hemin, iron protoporphyrin, and/or cobalt protoporphyrin.

HO-1 expression in a cell can be increased via gene transfer. As used herein, the term "express(ed)" means to cause increased production of a protein, e.g., HO-1 or ferritin, in isolated cells or the cells of a tissue, organ or animal using an exogenously administered gene (e.g., a recombinant gene). The HO-1 or ferritin is preferably of the same species (e.g., human, mouse, rat, etc.) as the recipient, in order to minimize any immune reaction. Expression could be driven by a constitutive promoter (e.g., cytomegalovirus promoters) or a tissue-specific promoter (e.g., milk whey promoter for mammary cells or albumin promoter for liver cells). An appropriate gene therapy vector (e.g., retrovirus, adenovirus, adeno associated virus (AAV), pox (e.g., vaccinia) virus, human immunodeficiency virus (HIV), the minute virus of mice, hepatitis B virus, influenza virus, Herpes Simplex Virus-1, and lentivirus) encoding HO-1 or ferritin would be administered to the patient orally, by inhalation, or by injection at a location appropriate for treatment intimal hyperplasia. Similarly, plasmid vectors encoding HO-1 or apo-ferritin can be administered, e.g., as naked DNA, in liposomes, or in microparticles.

Further, exogenous HO-1 protein can be directly administered to a patient by any method known in the art. Exogenous HO-1 can be directly administered in addition to, or as an alternative, to the induction or expression of HO-1 in the patient as described above. The HO-1 protein can be delivered to a patient, for example, in liposomes, and/or as a fusion protein, e.g., as a TAT-fusion protein (see, e.g., Becker-Hapak et al., Methods 24:247-256, 2001).

Alternatively or in addition, any of the products of metabolism by HO-1, e.g., bilirubin, biliverdin, iron, and/or ferritin, can be administered to a patient in conjunction with, or instead of, carbon monoxide in order to prevent or treat intimal hyperplasia. Further, the present invention contemplates that iron-binding molecules other than ferritin, e.g., desferoxamine (DFO), iron dextran, and/or apoferritin, can be administered to the patient. Further still, the present invention contemplates that enzymes (e.g., biliverdin reductase) that catalyze the breakdown any of these products can be inhibited to create/enhance the desired effect.

The present invention contemplates that compounds that release CO into the body after administration of the compound (e.g., CO-releasing compounds), e.g., dimanganese decacarbonyl, tricarbonyldichlororuthenium (II) dimer, and methylene chloride (e.g., at a dose of between 400 to 600 mg/kg, e.g., about 500 mg/kg) can also be used in the methods of the present invention, as can carboxyhemoglobin and CO-donating hemoglobin substitutes, and.

Administration any of the above can be administered to a patient in any way, e.g., by oral, intravenous, or intraarterial administration. Any of the above compounds can be administered to the patient locally and/or systemically, and in any combination.

The invention is illustrated in part by the following examples, which are not to be taken as limiting the invention in any way.

Example 1

CO Suppresses Arteriosclerosis, Development of Intimal Hyperplasia and SMC Proliferation Animals. Male (250-350 g) Brown Norway rats (RT1$^n$) were used as aortic graft donors and male (250-350 g) Lewis rats (RT1$_1$) as recipients. Dawley (400-450 g) rats were used in the balloon injury model. Adult male C57BL/6, C57/S129, p21$^{-/-}$ and p53$^{-/-}$ null mice were purchased from Jackson Laboratory (Bar Harbor, Me.). mkk3$^{(-/-)}$ null mice were generated as described Lu et al. (*EMBO*. 18:1845-1857 (1999)). The inos$^{-/-}$ and enos$^{-/-}$ mice were bred at the University of Pittsburgh.

Aortic transplant model. Aortic transplantation was performed as described in Shimizu et al. (Nat. Med. 7:738-741 (2001)). Briefly, 3 to 4 cm of descending aorta was harvested from the donor and implanted between the renal arteries and the aortic bifurcation of the recipient. Both edges of the native abdominal aorta were ligated.

Balloon injury model. Balloon angioplasty was carried out as described in Murakami et al. (Atherosclerosis 157:361-368 (2001)). Briefly, a 2 Fr. arterial embolectomy catheter (Baxter, Chicago, Ill.) was inserted into the common carotid artery, and injury was created by inflating the balloon to 5 atmospheres of pressure for 5 minutes. The arteries were flushed and the external carotid artery was ligated, ensuring return of blood flow through the common and internal carotid arteries. Injury of the vessel wall and subsequent pathological analysis was made in a manner that was blinded to the treatment group.

CO exposure. CO was delivered to animals as described in Otterbein et al. (Nat. Med. 6:422-428 (2000)). Graft donors and recipients were exposed to CO (250 ppm) for two days before transplantation and for 56 days immediately following transplantation. In the balloon injury model, rats received either no pretreatment or were exposed to CO (250 ppm) for one hour prior to injury. Following surgery rats were housed in room air for two weeks.

Cells. Primary mouse and rat smooth muscle cells (SMC) were isolated and cultured as described in Laubach et al. (Proc Natl Acad Sci USA 92:10688-9 (1995)). Mouse SMC isolated from HO-1$^{-/-}$ mice were obtained as described in Duckers et al. (*Nat. Med.* 7:693-698 (2001)).

Cell treatment and reagents. Guanylate cyclase inhibitor 1H(1,2,4) oxadiazolo(4,3-a)quinoxalin-1 (ODQ; Calbiochem-Novabiochem, San Diego, Calif.; 10-100 µM) and p38 MAPK inhibitor pyridinyl imidazol SB203580 (Calbiochem; 5-20 µM) were dissolved in DMSO. The cGMP analogue 8-bromo-cGMP sodium salt (8-Br-cGMP; Sigma-Aldrich, St. Louis, Mo.; 10-100 µM) and the PKG inhibitor (10-100 µM; Alexis Biochemicals) were dissolved in water.

Cell counts and [$^3$H] thymidine incorporation. Rat and mouse SMC were isolated and cultured as described in Peyton et al. (*Blood* 99:4443-4448 (2002)). Proliferation assays were carried out as described in Petkova et al. (*J Biol. Chem.* 276: 7932-7936 (2001)). For [$^3$H] thymidine incorporation studies, cells were serum-starved overnight and then stimulated with 10% serum containing 5 µCi/ml [$^3$H] thymidine (New England Nuclear, Boston Mass.). [$^3$H]thymidine incorporation was measured by scintillation spectroscopy and presented as mean counts/min/well.

Histomorphometric analysis. Aortic grafts and carotid arteries were harvested at 56 and 14 days respectively. Vessels were fixed, embedded, and serially sectioned (5µ) in toto. Every third slide was stained with Hematoxylin and Eosin (H&E) for histomorphometric analyses. In both models, one or two images per slide at a resolution of 1520×1080 pixels were captured at a magnification of 25× with a Zeiss microscope (Axioskop, Iowa City, Iowa), RT color SPOT (Diagnostic Instrument, Inc., Saint Joseph, Mich.) and Windows NT (Compaq Computer) using Adobe Photoshop version 5.5 software. Areas from eight to ten captured images were calculated using digital imaging software as number of pixels corresponding to those areas. Twenty-four to forty-eight sections from each group were statistically analyzed with SPSS software version 10.

Immunostaining and cell population histomorphometric analysis. Grafts were harvested 56 days after transplantation. Rat leukocyte populations were detected using anti-rat leukocyte common antigen (LCA, CD45; OX-1) (Serotec, Harlan Bioproducts, Indianapolis, Ind.); CD3 (G4.18), CD4 (OX-35), CD8 (OX-8) macrophage (CD68, ED-1), ICAM-1 (CD54; 1A29), and major histocompatibility class II (OX-6) were all obtained from Becton Dickinson Biosciences, (San Diego, Calif.). Anti-PAI-1 mAb was obtained from America Diagnostica (Greenwich, Conn.). Eight to ten images were captured from each transplanted aorta and analyzed as detailed above.

Cell extracts and Western Blot Analysis. Cellular protein extracts were electrophoresed (10-12.5% polyacrylamide gels) and transferred onto nitrocellulose (BioRad, Hercules, Calif.). Total and phosphorylated forms of ERK, JNK and p38 MAPK as well as ATF-2 were detected using rabbit polyclonal antibodies (Cell Signaling Technologies, Beverly, Mass.). Anti α-actin (Sigma; St. Louis, Mo.). p21$^{Cip1}$ was detected using a rabbit polyclonal antibody (Santa Cruz Biotech, Santa Cruz, Calif.). Primary antibodies were detected as described in supplementary methods.

Statistical Analysis. The significance of difference was determined using analysis of variance (ANOVA).

Nitric Oxide (NO) exposure. Rats were exposed to 250 ppm or 500 ppm NO for 1 hour. NO gas (1% in N2) was mixed with air in the same exposure apparatus as used in the CO experiments. Concentrations in the chamber were monitored with an NO analyzer (Interscan). Following exposure, balloon angioplasty was carried out as described above. Control animals were exposed to air. The surgeon inflicting the balloon injury was blinded to the rats being manipulated. Analyses of carotid arteries was performed 2 weeks after the procedure as described above.

Mouse arterial injury. The dissection was similar to that described by Lindner et al. (*Circ Res.* 73:792-796 (1993)), and was performed using a 0.018 inch guide wire (Cook, Bloomington, Ind.), inserted through an external carotid arteriotomy into the common carotid, rotated 360 degrees three times and removed a total of three consecutive times.

cGMP immunoassays. Cellular levels of cGMP were quantified using an EIA (Biomol, Plymouth Meeting, Pa.). SMC were incubated in the presence or absence of CO (250 ppm) and cell lysates were analyzed for cGMP content, as suggested by the vendor.

Cell Counts. Cells were seeded at $5 \times 10^3$ cells/well and cultured overnight in high glucose DMEM containing 10% FCS, penicillin, and gentamicin (Life Technologies). Cells were serum starved for an additional 48 hours (0% serum) and where indicated exposed to CO (250 ppm for rat and mouse SMC) before induction of cell proliferation (10% FCS; Life Technology). Cells were counted daily using a Neubauer hemocytometer. Viability was assessed with trypan blue.

Recombinant adenovirus. Recombinant β-galactosidase adenovirus was obtained from the University of Texas Southwest Medical Center, Dallas, Tex. Recombinant HO-1 adenovirus expressing the rat HO-1 cDNA has been described in Brouard et al. (*J Exp Med.* 192:1015-1026 (2000)). Rat SMC were infected with a multiplicity of infection (MOI) of 400 plaque forming units per cell (PFU/cell), as described in Brouard et al. (Id.).

Flow Cytometry. Rat aortic SMC were harvested by trypsin digestion (0.025% Trypsin/0.01% EDTA) (Life Technology), washed in phosphate buffered saline (PBS, pH 7.2) with 0.5% bovine serum albumin (BSA; Sigma-Aldrich Co), and incubated with Propidium iodide (1 μg/ml, 1 h, RT). Fluorescent labeling was evaluated using a FACsort equipped with Cell Quest Software (Becton Dickinson, Palo Alto, Calif.). Experiments were carried out in triplicate.

Histomorphometric analyses. In the transplant model, grafts were harvested 56 days after transplantation. Aortas were fixed in 10% formalin, embedded in paraffin and serially sectioned (5μ) in toto. Ten samples from every three sections were placed per slide in a total of about twenty-four to thirty slides. Every third slide was stained with Hematoxylin and Eosin (H&E) for histomorphometric analysis. In the balloon injury model, animals were euthanized 14 days following injury and arteries were collected for morphometric analysis. Rat carotid arteries were perfused and fixed in situ with PBS and paraformaldehyde (2%). Vessels were fixed for 2 hours in 2% paraformaldehyde at 4° C. and cryoprotected in 30% sucrose overnight at 4° C. Vessels were quick-frozen in 2-methylbutane and 7 μm cryosections were cut.

Primary Antibody Detection for Immunoblotting. Primary antibodies were detected using horseradish peroxidase conjugated anti-rabbit IgG secondary antibodies (Pierce, Rockford, Ill., USA). Peroxidase was visualized using the Enhanced ChemiLuminescence assay (Amersham Life Science Inc., Arlington Heights, Ill., USA), according to manufacturer's instructions and stored in the form of photoradiographs (BiomaxTMMS, Eastman Kodak, Rochester, N.Y.). Where indicated, membranes were stripped (62.5 mM Tris.HCl pH 6.8, 2% SDS and 100 mM β-mercaptoethanol, 30 minutes, 50° C.). Phosphorylated p38 were normalized to the total amount of p38, detected in the same membrane.

Miscellaneous Reagents. Mouse iNOS and eNOS were detected using rabbit anti-mouse polyclonal antibodies against iNOS and eNOS (Becton Dickinson, Biosciences, San Diego, Calif.).

CO Suppresses the Development of Transplant-Associated Arteriosclerosis.

Figure 1B:
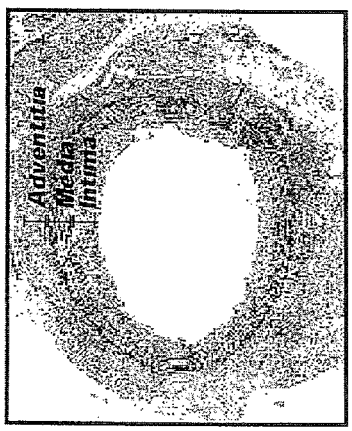
FIG. 1B is a photomicrograph (50× magnification) of an allogeneically transplanted aortic graft illustrating the effect of allogeneic transplantation on the graft.
Figure 1C:
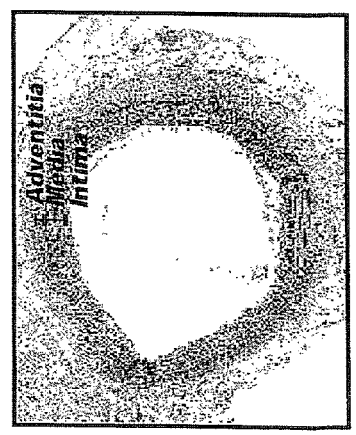
FIG. 1C is a photomicrograph (50× magnification) of an allogeneically transplanted aortic graft illustrating the effect of allogeneic transplantation on the graft when the recipient is exposed to CO.
Figure 1D:
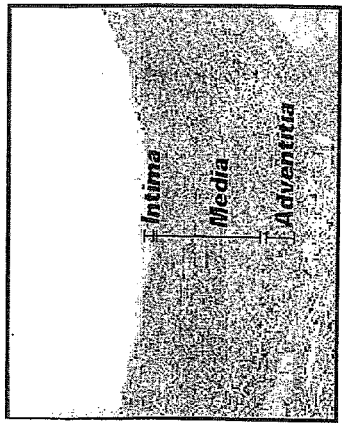
FIG. 1D is a photomicrograph (200× magnification) of a syngeneically transplanted aortic graft illustrating the effect of syngeneic transplantation on the graft.
Figure 1E:
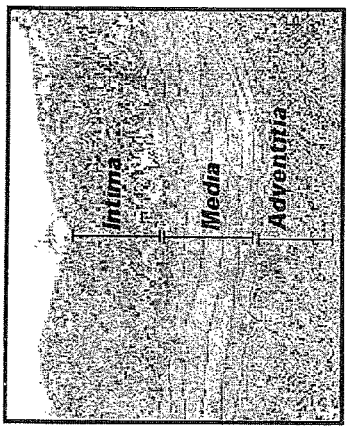
FIG. 1E is a photomicrograph (200× magnification) of an allogeneically transplanted aortic graft illustrating the effect of allogeneic transplantation on the graft.
Figure 1F:
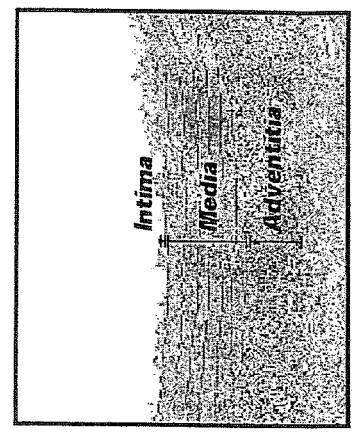
FIG. 1F is a photomicrograph (200× magnification) of an allogeneically transplanted aortic graft illustrating the effect of allogeneic transplantation on the graft when the recipient is exposed to CO.
Figure 1I:
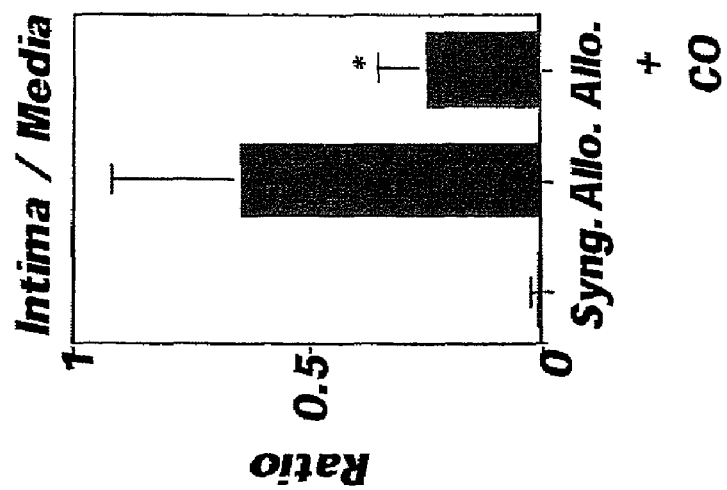
FIG. 1I is a bar graph illustrating the intima/media area ratio of aortic grafts transplanted syngeneically into air-exposed recipients (Syng.), allogeneically into air-exposed recipients (Allo.), and allogeneically into CO-exposed recipients (Allo.+CO).
Figure 1H:
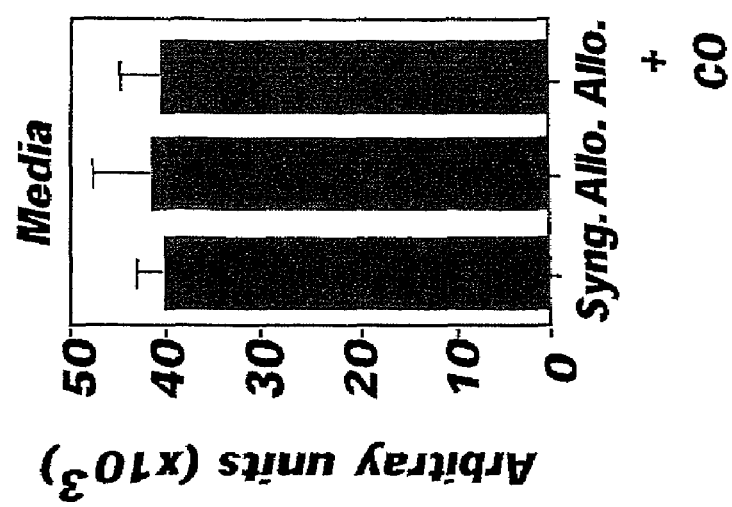
FIG. 1H is a bar graph illustrating the mean relative areas (in arbitrary units) of the media of aortic grafts transplanted syngeneically into air-exposed recipients (Syng.), allogeneically into air-exposed recipients (Allo.), and allogeneically into CO-exposed recipients (Allo.+CO).
Figure 1G:
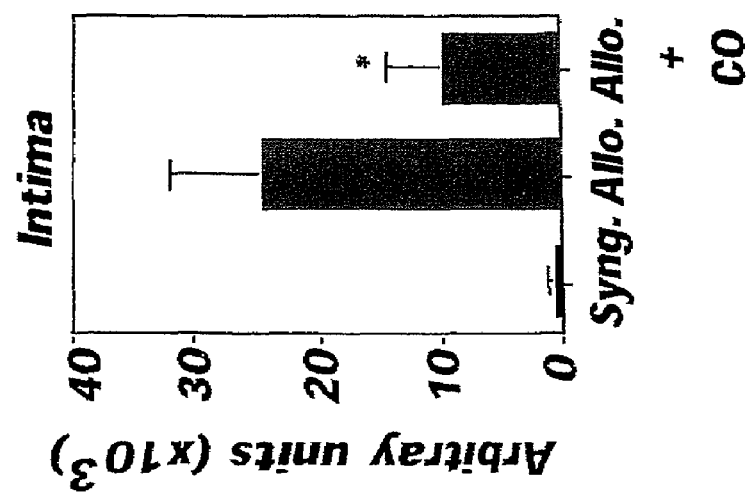
FIG. 1G is a bar graph illustrating the mean relative areas (in arbitrary units) of the intima of aortic grafts transplanted syngeneically into air-exposed recipients (Syng.), allogeneically into air-exposed recipients (Allo.), and allogeneically into CO-exposed recipients (Allo.+CO).

FIGS. 1A-1I illustrate that CO treatment suppresses intimal hyperplasia normally associated with chronic graft rejection. FIGS. 1A-1F are photomicrographs of samples of various aortic grafts 56 days after transplantation. To generate these data, Brown Norway aortas were transplanted into Brown Norway rats (FIGS. 1A and 1D), Lewis rats exposed to air (FIGS. 1B and 1E), and Lewis rats exposed to CO (250 ppm; FIGS. 1C and 1F). Samples were harvested 56 days after transplantation and stained by a modified elastic tissuemasson trichrome (elastic; FIGS. 1A-1C) or by hematoxylin and eosin (H&E; FIGS. 1D-1E). Elastic stainings are magnified 50× (FIGS. 1A-1C) and H&E stainings are magnified 200× (FIGS. 1D-1E). Samples shown are representative of 3-6 animals analyzed per group. FIGS. 1G-1I are bar graphs illustrating the mean (±standard deviation) relative areas corresponding to the intima and media regions, calculated from samples harvested from Brown Norway aortas transplanted into Brown Norway rats (Syng.; n=6), Lewis rats exposed to air (Allo.; n=6) or CO (250 ppm) (Allo.+CO; n=3). *P<0.001 versus Allo.+CO.

Brown Norway aortic segments transplanted into Lewis rats developed arteriosclerotic lesions consistent with chronic graft rejection (FIGS. 1B and 1E). The lesions appeared 20-30 days after transplantation but were significantly more pronounced by 50-60 days; all analyses were carried out 56 days following transplantation. The lesions were characterized by intimal hyperplasia, loss of medial SMC, and leukocyte accumulation in the adventitia (FIGS. 1B and 1E). These characteristics were not observed in vessels of the recipient, and the lesions were not observed in syngeneic grafts (FIGS. 1A and 1D). Intimal hyperplasia was significantly (p<0.001) inhibited (61.4±12.9% reduction versus control) in aortas transplanted into recipients exposed to CO (250 ppm) immediately after transplantation (and for 56 days thereafter), as compared to those transplanted into air-exposed recipients (FIGS. 1C, 1F, 1G, 1H, an 1I).

Figure 2A:
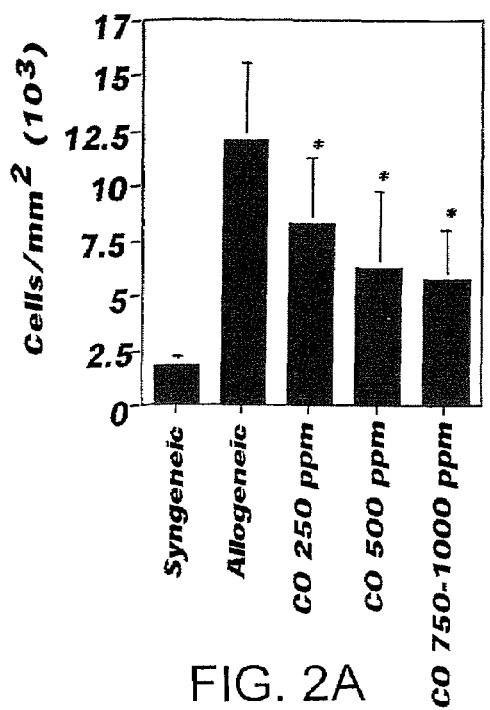
FIG. 2A is a bar graph illustrating accumulation of activated leukocytes (measured by counting total nuclei) in the adventitia of aortic grafts transplanted syngeneically into air-exposed recipients (Syngeneic), allogeneically into air-exposed recipients (Allogeneic) and allogeneically into recipients exposed to various concentrations of CO(CO 250 ppm; CO 500 ppm; and CO 750-1000 ppm).
Figure 2B:
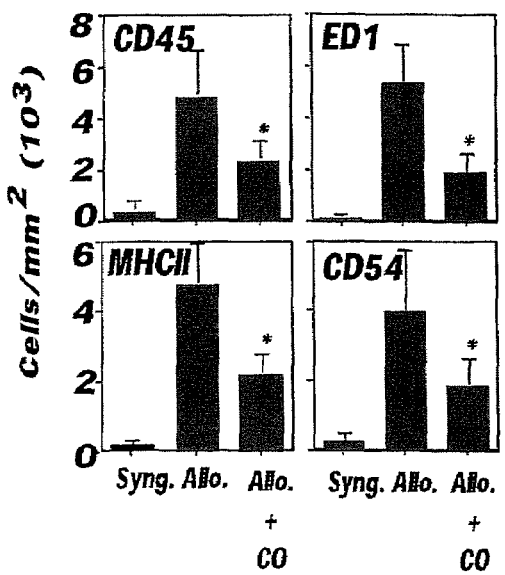
FIG. 2B is a set of bar graphs illustrating accumulation of CD45, ED1, MHCII, and CD54 positive cells in the adventitia of aortic grafts transplanted syngeneically into air-exposed recipients (Syng.), allogeneically into air-exposed recipients (Allog.), and allogeneically into CO-exposed recipients (Allo.+CO).
Figure 2C:
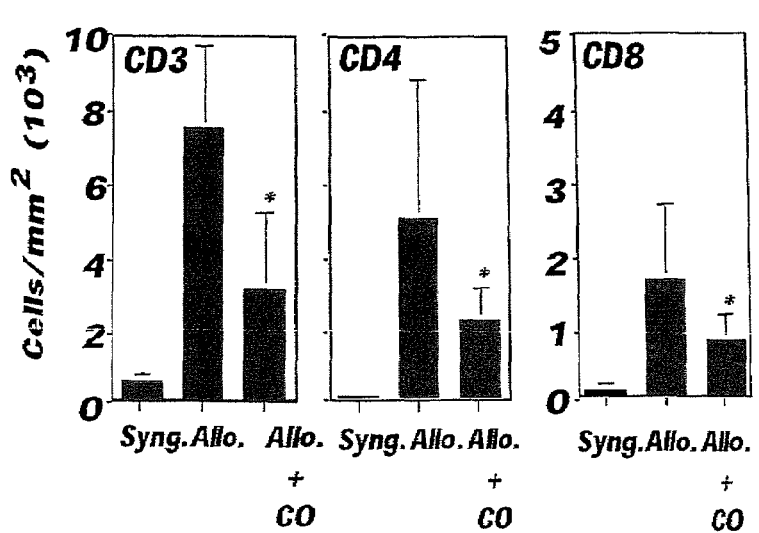
FIG. 2C is a set of bar graphs illustrating accumulation of CD3, CD4, and CD8 positive cells in the adventitia of aortic grafts transplanted syngeneically into air-exposed recipients (Syng.), allogeneically into air-exposed recipients (Allog.), and allogeneically into CO-exposed recipients (Allo.+CO).

FIGS. 2A-C are bar graphs illustrating that CO suppresses graft infiltration by activated leukocytes. To generate the data in FIGS. 2A-2C, immunocytochemical analyses were performed on aortic grafts 56 days after transplantation. Brown Norway rat aortas were transplanted into Brown Norway rats (syngeneic), untreated Lewis rats (allogeneic) or Lewis rats exposed to CO (250-1000 ppm). Samples were harvested 56 days after transplantation. FIG. 2A illustrates the mean (±standard deviation (n=3-6)) number of nuclei in the adventitia from Brown Norway aortas transplanted into Brown Norway recipients (Syngeneic), untreated Lewis recipients (Allogeneic), and Lewis recipients exposed to various concentrations of CO(CO 250 ppm, CO 500 ppm, and CO 750-1000 ppm) (*=P<0.001 versus Allo.). FIG. 2B illustrates the mean (±standard deviation (n=6)) number of CD45 (*P<0.002 versus Allo.), CD68 (Mø/ED1; *P<0.001 versus Allo.), MHC II, and CD54 (ICAM-1) positive cells (*P<0.001 versus Allo.) in the adventitia from Brown Norway rat aortas transplanted into Brown Norway rat recipients (Syng.), untreated Lewis rat recipients (Allo.), and Lewis rat recipients exposed to CO (Allo.+CO). FIG. 2C illustrates the mean (±standard deviation (n=6)) number of CD3, CD4, and CD8 positive cells (*P<0.02, 0.001, 0.096 respectively versus Allo.) in the adventitia from Brown Norway aortas transplanted into Brown Norway recipients (Syng.), untreated Lewis recipients (Allo.), and Lewis recipients exposed to CO(CO 250 ppm).

Accumulation of leukocytes in the adventitia of transplanted aortas was inhibited in CO-exposed recipients (see FIGS. 2A-2C). Leukocyte accumulation was not observed in syngeneic grafts. The ability of CO to suppress graft infiltration by activated leukocytes (CD45+) was dose dependent with increasing levels of CO (250-1000 ppm) resulting in decreased leukocyte infiltration; a maximal effect was observed at 700 to 1000 ppm of CO (52±20% inhibition versus air treated controls FIG. 2A). CO significantly suppressed the accumulation of CD45+/CD68+ monocyte/macrophages (Mø) (65±24% inhibition versus air treated controls) as well as CD45+/CD3+ T cells (57±22% inhibition versus air treated controls), including both CD4+ ("helper") and CD8+ ("cytotoxic") cells (FIG. 2C). CO also inhibited expression of pro-inflammatory genes associated with Mø activation including the major histocompatibility class II (MHC II) antigens and the intracellular adhesion molecule 1 (CD54/ICAM-1) (FIG. 2B).

CO Suppresses Development of Intimal Hyperplasia after Balloon Injury.

Figure 3A:
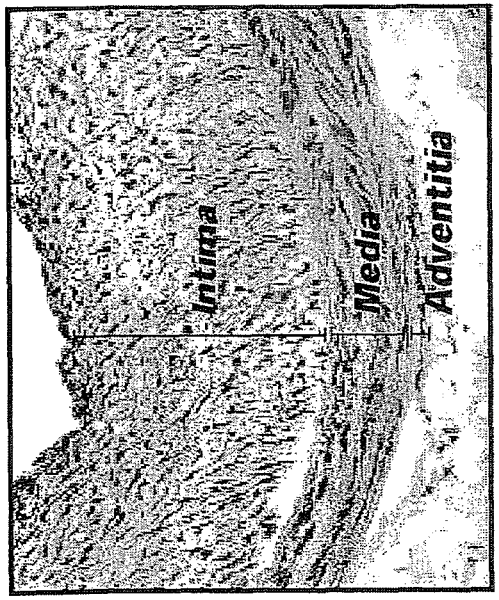
FIG. 3A is a photomicrograph (10× magnification) of a carotid artery sample illustrating the effect of balloon angioplasty on the artery.
Figure 3C:
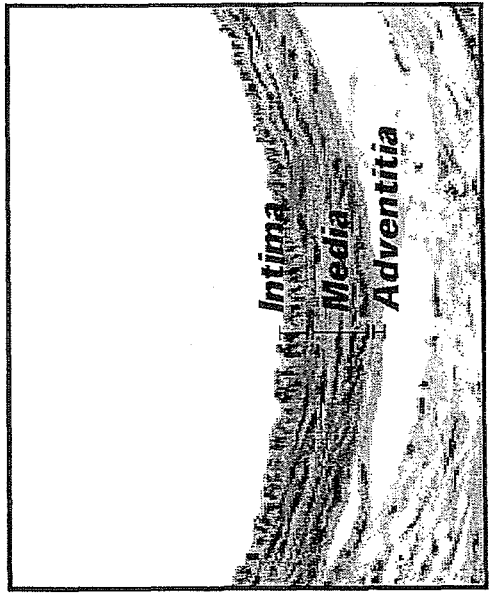
FIG. 3C is a photomicrograph of a carotid artery sample illustrating the effect of balloon angioplasty on the artery.
Figure 3B:
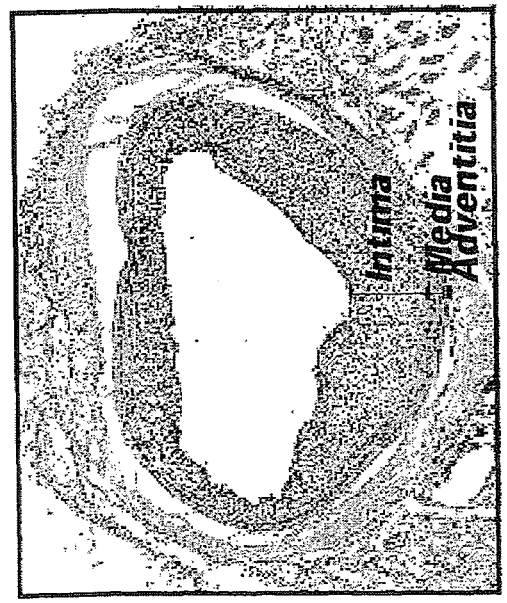
FIG. 3B is a photomicrograph (10× magnification) of a carotid artery sample illustrating the effect of balloon angioplasty on the artery when the subject is pre-exposed to CO.
Figure 3D:
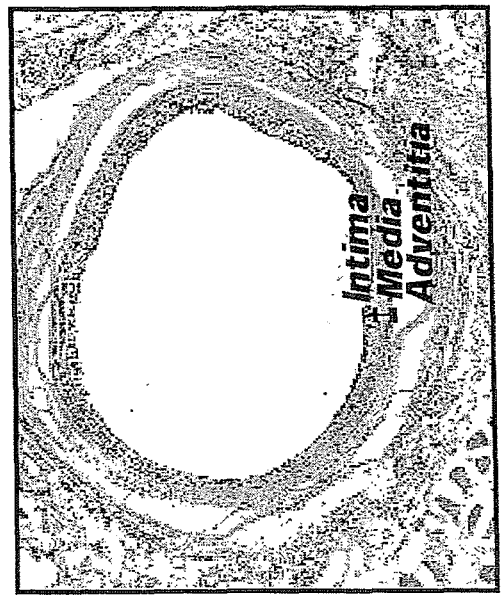
FIG. 3D is a photomicrograph of a carotid artery sample illustrating the effect of balloon angioplasty on the artery when the subject is pre-exposed to CO.
Figures 3E, 3F, 3G:
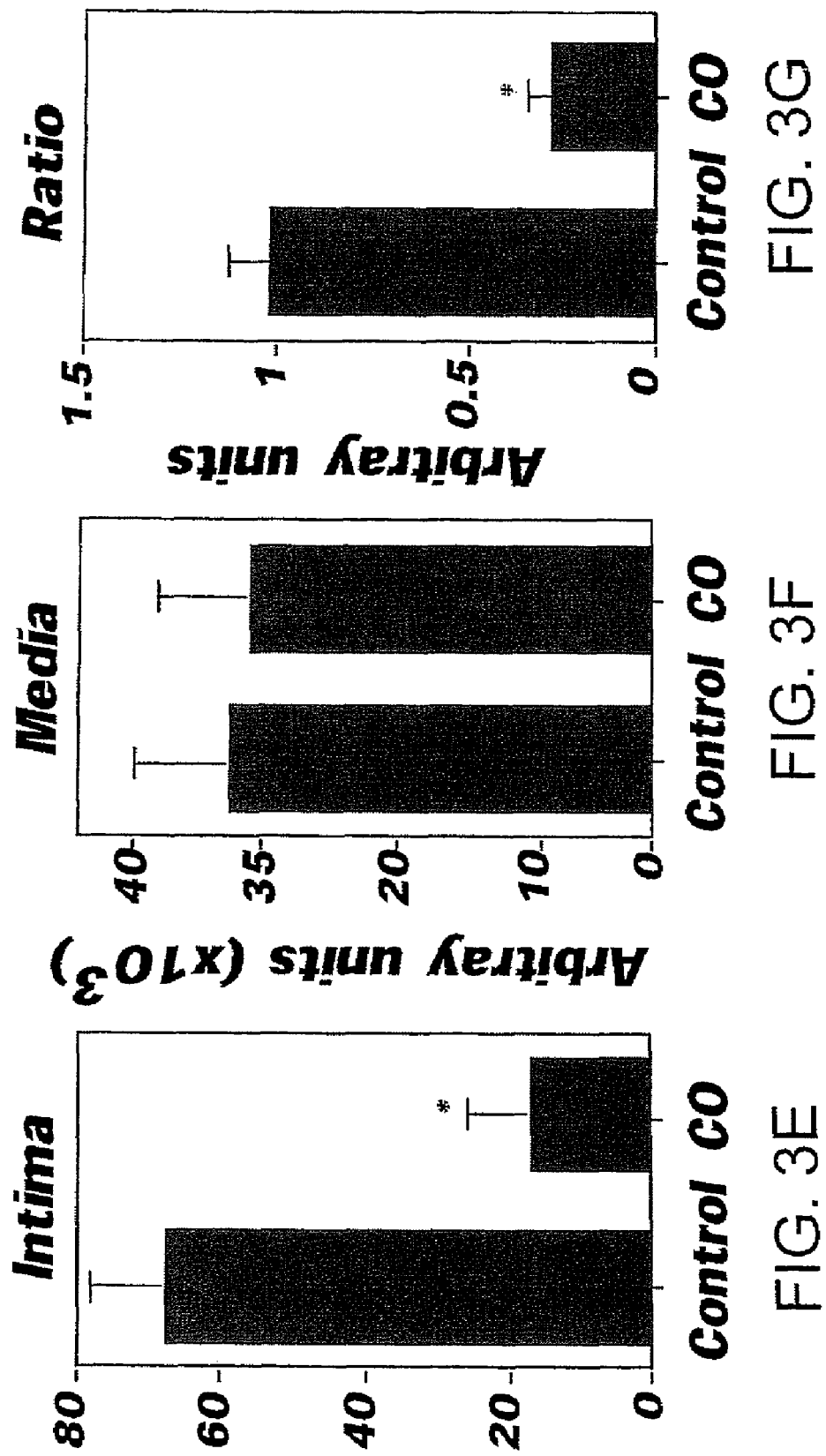
FIG. 3E is a bar graph illustrating the mean relative areas (in arbitrary units) of the intima of carotid arteries subjected to balloon angioplasty when the subject animal is pre-exposed either to air (Control) or 250 ppm CO (CO).
FIG. 3F is a bar graph illustrating the mean relative areas (in arbitrary units) of the media of carotid arteries subjected to balloon angioplasty when the subject animal is pre-exposed either to air (Control) or 250 ppm CO (CO).
FIG. 3G is a bar graph illustrating the intima/media area ratio of carotid arteries subjected to balloon angioplasty when the subject animal is pre-exposed either to air (Control) or 250 ppm CO (CO).

FIGS. 3A-3G illustrate that CO suppresses the development of vascular lesions associated with balloon injury. FIGS. 3A-3D are photomicrographs (10× magnification) of immunocytochemically stained carotid arteries analyzed 14 days after balloon angioplasty. To generate the data in FIGS. 3A-3D, rats were exposed to room air (FIGS. 3A and 3C) or to CO (1 hour; 250 ppm; FIGS. 3B and 3D) prior to balloon injury. All animals were exposed to room air following balloon injury. Two weeks after balloon injury, samples were stained with hemotoxylin and eosin (H&E). Samples from room air (FIGS. 3A and 3C) and CO pretreated rats (FIGS. 3B and 3D) are shown. FIGS. 3E, 3F, and 3G are bar graphs illustrating the mean (±standard deviation (n=8; *P<0.001 versus control)) relative areas of the intima and media regions of samples analyzed in FIGS. 3A-3D.

Rat carotid arteries developed intimal hyperplasia 14 days after balloon injury (FIGS. 3A and 3C; and FIGS. 3E-3G). Intimal hyperplasia in rats exposed to CO (250 ppm) for one hour prior to balloon injury (after which CO exposure was discontinued) was suppressed by 74±8% as compared to control animals exposed to air (n=8-10; p<0.001) (FIGS. 3B and 3D and FIGS. 3E-3G).

CO Suppresses SMC Proliferation.

Figure 4D:
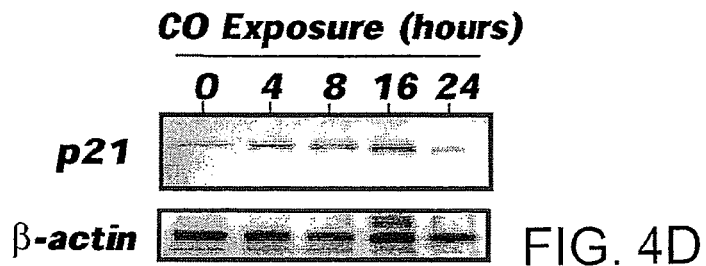
FIG. 4D is a Western blot illustrating the effect of CO exposure (for 0, 4, 5, 16, and 24 hours) on p21 and β-actin protein expression in mouse SMC.

FIGS. 4A-4F illustrate that CO blocks SMC proliferation and that $p21^{Cip1}$ is involved in the anti-proliferative effect of CO in vitro. FIG. 4A is a line graph illustrating proliferation of rat SMC that were non-transduced (○; Medium), or transduced with Lac.Z (□; LacZ Rec. Ad.) or HO-1 (●; HO-1 rec. Ad.) recombinant adenovirus. Results shown are mean±standard deviation of n=3 wells per group (*P<0.001 versus LacZ and non-transduced). FIG. 4B is a line graph illustrating proliferation of rat SMC growth in the presence or absence of CO (●; 1000 ppm). Results shown are mean±standard deviation (n=3 wells per group; P<0.001 versus air, □). FIG. 4C is a bar graph illustrating proliferation of $SMC_1$ isolated from wild type (WT) or HO-1 deficient (ho-$1^{-/-}$) mice in the presence and absence of CO (250 ppm) (n=6 wells/group; #P<0.006 versus air, *P<0.001). FIG. 4D is a Western blot illustrating p21 and β-actin protein expression in mouse SMC following exposure to CO (250 ppm). FIG. 4E is a bar graph illustrating proliferation of mouse SMC isolated from wild type (wt), $p21^{Cip1}$ (p21-/-) or p53 (p53-/-) deficient mice. Gray bars indicate cells exposed to room air and black bars indicate cells exposed to CO (250 ppm). Results shown are the mean±standard deviation (n=3*P<0.001 versus air) in one out of 6 independent experiments. FIG. 4F is a bar graph illustrating that endogenous expression of $p21^{Cip1}$ plays a critical role in controlling the extent of intimal hyperplasia following arterial injury in mice. Wild type (C57/B16/S129) or p21-/- mice were exposed to room air or CO (1 hour; 250 ppm) before carotid artery injury and exposed to room air thereafter. Samples were harvested and analyzed two weeks after injury. Mean±standard deviation (n=4) of the ratio between the relative area of the intima and media is expressed in arbitrary units (*P<0.001 versus air).

Figure 7A:
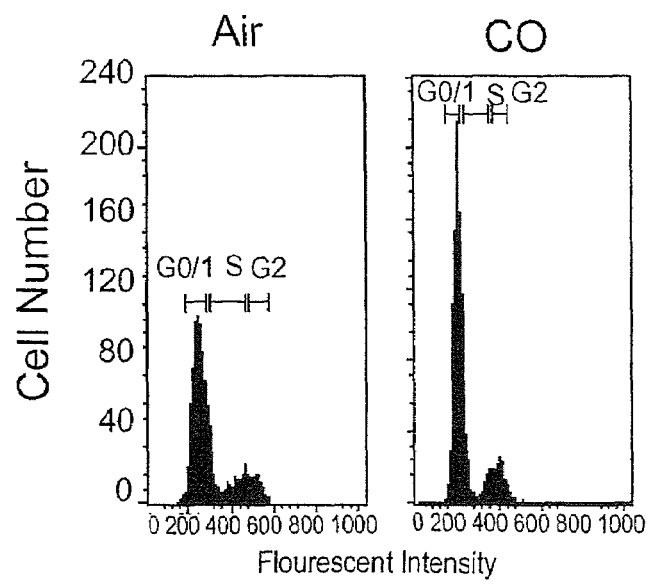
FIG. 7A is a flow cytometry plot illustrating the effect of air (Air) and CO (250 ppm) exposure on the cell cycle of rat aortic SMC.
Figure 7B:
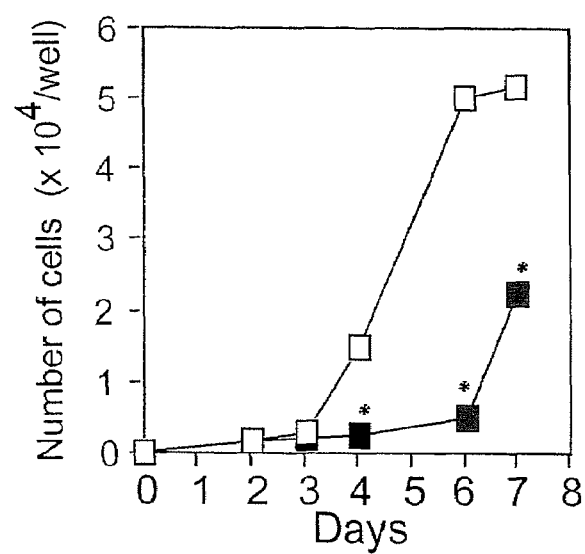
FIG. 7B is a line graph illustrating the effect of air (□) and CO (■) on SMC proliferation.

FIGS. 7A-7B further illustrate that CO blocks SMC proliferation. FIG. 7A is a cell cycle analysis of rat aortic SMC in standard incubation (Air) versus CO (250 ppm) after 24 hours of treatment. Results shown are representative of 3 independent experiments. FIG. 7B is a line graph illustrating SMC proliferation in the presence (■; CO, 250 ppm) or absence (□; air) of CO for 6 days. SMC were serum stimulated on day 3 of the experiment. Proliferation increased in CO-treated SMC after CO exposure was discontinued on day 6. Results shown are representative of 3 independent experiments, each performed in triplicate (*P<0.01 vs Air).

Figure 8:
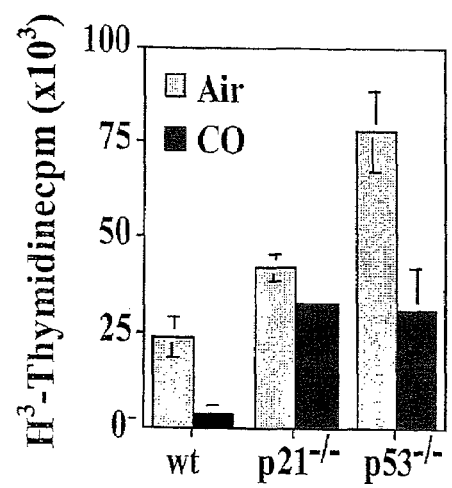
FIG. 8 is a bar graph illustrating [$^3$H]thymidine uptake by wild type (wt), p21$^{-/-}$, and p53$^{-/-}$ mouse SMC exposed to either air (gray bars) or to CO (250 ppm; black bars) for 24 hours.

FIG. 8 is a bar graph illustrating that CO blocks SMC proliferation from wild type (wt) and $p53^{-/-}$ mice but not from $p21^{-/-}$ mice. The figure presents the results of a [$^3$H] thymidine incorporation assay used to assess cellular proliferation (counts per minute; cpm) in wild type (wt), $p21^{-/-}$, and $p53^{-/-}$ mouse SMCs exposed to air (gray bars) or to CO (250 ppm; black bars) for 24 hours. Results shown are the mean±standard deviation (n=3; *P<0.05 versus air).

Figure 9A:
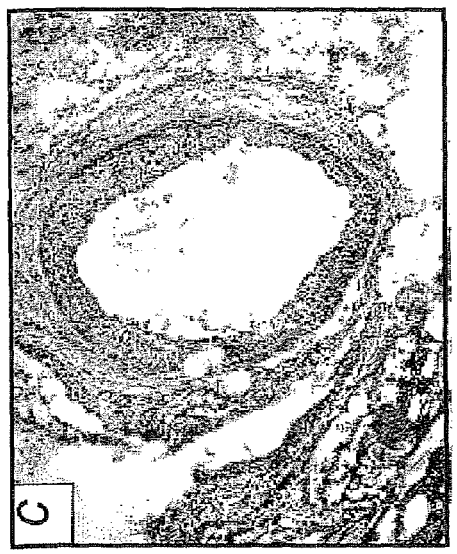
FIG. 9A is a photomicrograph (20× magnification) of a carotid artery section from a wild type mouse 14 days after wire injury. The subject animal was exposed to room air for 1 h prior to wire injury.
Figure 9C:
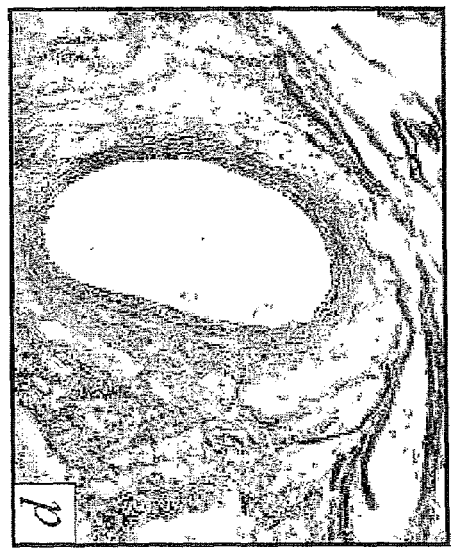
FIG. 9C is a photomicrograph (20× magnification) of a carotid artery section from a p21$^{-/-}$ mouse 14 days after wire injury. The subject animal was exposed to room air for 1 h prior to wire injury.
Figure 9B:
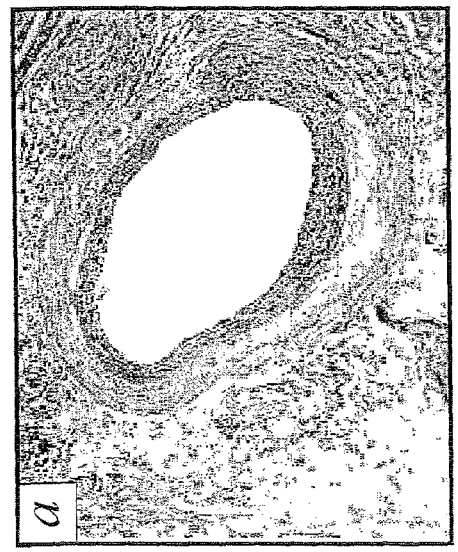
FIG. 9B is a photomicrograph (20× magnification) of a carotid artery section from a wild type mouse 14 days after wire injury. The subject animal was exposed to CO (250 ppm) for 1 h prior to wire injury.
Figure 9D:
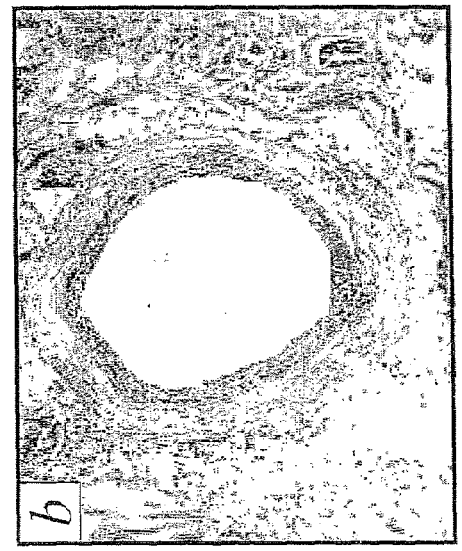
FIG. 9D is a photomicrograph (20× magnification) of a carotid artery section from a p21$^{-/-}$ mouse 14 days after being subjected to wire injury. The subject animal was exposed to CO (250 ppm) for 1 h prior to wire injury.

FIGS. 9A-9G illustrate that CO suppresses the development of vascular lesions associated with wire injury in wild type (C57/B16/S129) and $p21^{-/-}$ mice. FIGS. 9A-9D are photomicrographs (20× magnification) of immunocytochemically stained carotid arteries 14 days following wire injury. Mice were exposed to room air (FIGS. 9A and 9C) or CO (1 hour; 250 ppm; FIGS. 9B and 9D) prior to wire injury. All animals were exposed to room air following injury. Two weeks after wire injury, samples were stained with hemotoxylin and eosin (H&E). Samples from wild type (FIGS. 9A and 9B) and $p21^{-/-}$ (FIGS. 9C and 9D) mice are shown. FIGS. 9E, 9F, and 9G are bar graphs illustrating the Mean (±standard deviation (n=4*P<0.001 versus control)) relative areas corresponding to the intima and media regions, as well as intima:media ratios, from the photomicrographs shown in FIGS. 9A-9D.

CO Suppresses SMC Proliferation In Vitro

An in vitro system was used to evaluate SMC growth in the presence or absence of CO to delineate the mechanism by which CO inhibited intimal hyperplasia. Serum starved SMC proliferated upon re-addition of serum to culture medium (FIG. 7B); control SMC not exposed to serum exhibited minimal proliferation during the five days of the experiment. Expression of a HO-1 recombinant adenovirus or exposure to CO suppressed SMC proliferation (FIGS. 4A and 4B). In a similar system, "scavenging" of CO by hemoglobin suppressed the anti-proliferative effect of HO-1, suggesting that CO generated by HO-1 likely accounts for the anti-proliferative effect of HO-1. Cell cycle analysis revealed that SMC treated with CO accumulated in the G0/G1 phase (FIG. 7A). SMC from mice that lack HO-1 (ho-$1^{-/-}$) proliferated significantly more rapidly when exposed to serum than did SMC from wild type mice (FIG. 4C), indicating that endogenous HO-1 expression in SMC exposed to serum suppresses smooth muscle cell proliferation. CO significantly inhibited proliferation of SMC from ho-$1^{-/-}$ mice, suggesting that CO accounts in large measure for the anti-proliferative action of HO-1. Inhibition of SMC proliferation was not associated with cell death as assessed by trypan blue and propidium iodide exclusion analyses. The anti-proliferative effects of CO were reversible, as cessation of CO exposure allowed SMC to begin to proliferate again (FIG. 7B).

The In Vitro Anti-Proliferative Effect of CO Depends on $p21^{Cip1}$.

SMC exposed to CO up-regulated p21$^{Cip1}$ protein expression (FIG. 4D), similar to SMC that overexpressed HO-1. This effect was transitory in that p21$^{Cip1}$ expression increased significantly by 4 hours, was maximal by 16 hours and returned to basal levels at 24 hours after CO exposure (FIG. 4D). Proliferation of SMC from p21$^{Cip1}$ deficient mice (p21$^{-/-}$) was not suppressed by CO (FIG. 4E), indicating that p21$^{Cip1}$ expression is required for the anti-proliferative effect of CO. Despite the established role of p53 in regulation of p21$^{Cip1}$ expression, CO induced p21$^{Cip1}$ expression and inhibited proliferation of SMC derived from p53$^{-/-}$ or from wild type mice to a similar extent (FIG. 4E and FIG. 8). Thus, the anti-proliferative effect of CO in vitro is dependent on p21$^{Cip1}$ expression, which does not involve p53.

Involvement of p21$^{Cip1}$ in the In Vivo Anti-Proliferative Effect of CO p21$^{Cip1}$ is expressed following vascular wall injury, likely functioning to regulate SMC proliferation and the development of intimal hyperplasia. The role of endogenous p21$^{Cip1}$ expression on development of intimal hyperplasia following arterial injury in mice was investigated. Intimal hyperplasia was three times more pronounced in air treated p21$^{-/-}$ mice than in wild-type mice (n=4; 314±41.8%, p<0.001), showing that endogenous expression of p21$^{Cip1}$ plays a critical role in controlling the extent of intimal hyperplasia following arterial injury in mice (FIG. 4F). In contrast, one hour of CO (250 ppm) pre-treatment suppressed intimal hyperplasia in both wild-type (C57/S129) and p21$^{-/-}$ (C57/S129) mice by 80.9±7.2% (n=4, p<0.001) and 86.2±14% (n=4, p<0.001), respectively, versus air treated controls (FIG. 4F; FIGS. 9A-9G). Thus, in this in vivo mouse model, CO suppresses intimal hyperplasia via a mechanism that is not dependent on the expression of p21$^{Cip1}$.

The Anti-Proliferative Effect of CO Requires Activation of Guanylate Cyclase and Generation of cGMP, and is Exerted Via Activation of p38 MAPK.

Figure 5C:
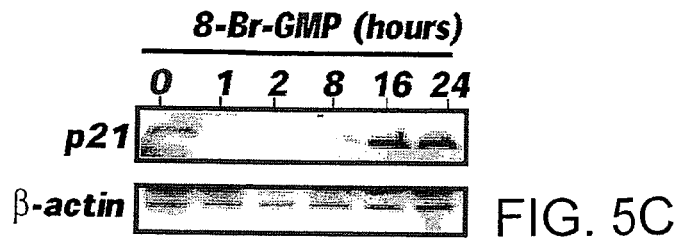
FIG. 5C is a composite picture of a Western blot illustrating the effect of 8-Bromoguanosine 3'-5'-cyclic monophosphate sodium salt (8-Br-cGMP) on p21$^{Cip1}$ expression.
Figure 5E:
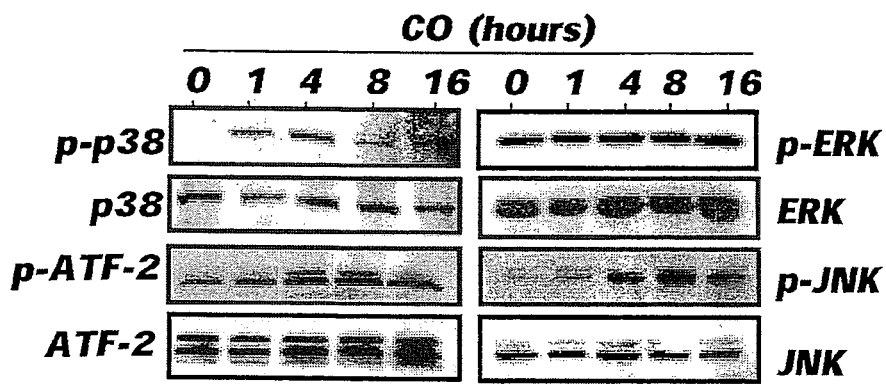
FIG. 5E is a composite picture of a Western blot illustrating the effect of CO (250 ppm) on expression of phosphorylated p38 MAPK (p-p38), ATF-2 (p-ATF-2), JNK (p-JNK) and ERK (p-ERK) as compared to total p38 MAPK, ATF-2, JNK, and ERK in SMC.
Figure 5G:
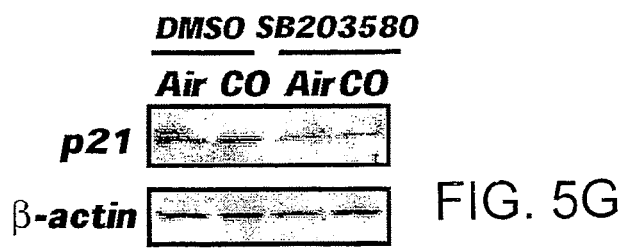
FIG. 5G is a composite picture of a Western blot illustrating the effect of air (Air), CO (250 ppm; CO)), SB203580, and DMSO on expression of p21$^{Cip1}$ in mouse SMC.
Figure 5A:
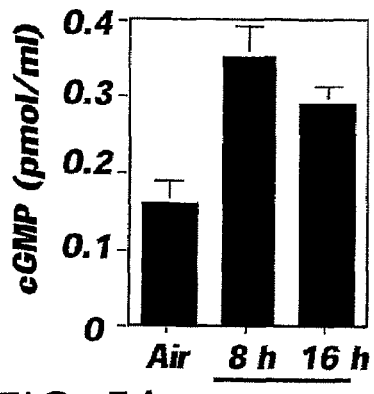
FIG. 5A is a bar graph illustrating the effect of air (Air) and CO (250 ppm for 8 h or 16 h) exposure on the mean cellular cGMP content of mouse SMCs.
Figure 5B:
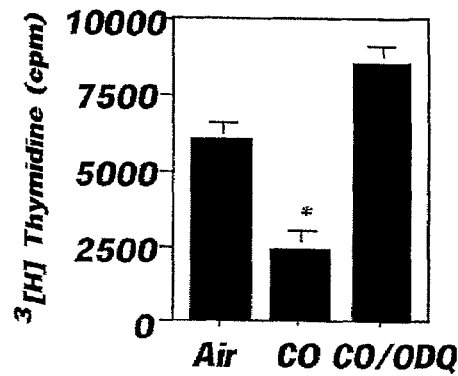
FIG. 5B is a bar graph illustrating [$^3$H]thymidine uptake by mouse SMCs exposed to air (Air), CO (250 ppm) and CO plus the guanylate cyclase inhibitor 1H(1,2,4) Oxadiazolo(4,3-a) Quinoxalin-1 (CO/ODQ).
Figure 5D:
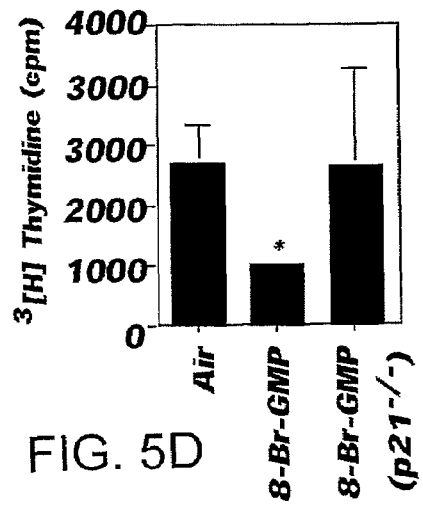
FIG. 5D is a bar graph illustrating [$^3$H]thymidine uptake by SMC isolated from wild type (wt) and p21$^{Cip1}$ (p21$^{-/-}$) deficient mice in the presence (8Br-cGMP; 8Br-cGMP (p21$^{-/-}$)) and absence (Air) of the cGMP analogue 8Br-cGMP.
Figure 5F:
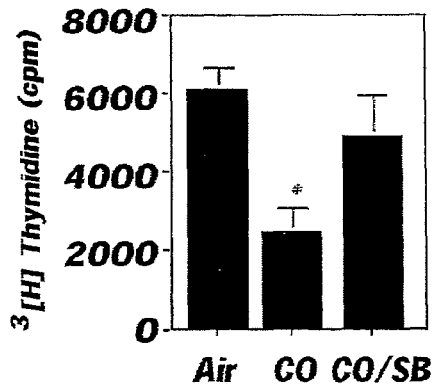
FIG. 5F is a bar graph illustrating [$^3$H]thymidine uptake by mouse SMC exposed air (Air) 250 ppm CO(CO) and CO plus the p38 MAPK inhibitor SB203580 (CO/SB).

FIGS. 5A-5G illustrate that CO blocks SMC proliferation via generation of cGMP and activation of p38 MAPK. FIG. 5A is a bar graph illustrating the mean (±standard deviation (n=3)) cellular cGMP content in mouse SMC exposed to air or CO (250 ppm for 8 h or 16 h). FIG. 5B is a bar graph illustrating the results of a [$^3$H]thymidine incorporation assay used to assess cellular proliferation (counts per minute; cpm) in mouse SMC exposed to CO (250 ppm) in the presence or absence of the guanylate cyclase inhibitor ODQ. Results shown are the mean standard deviation (n=3; *P<0.05 versus air and CO/ODQ). FIG. 5C is a picture of a Western blot of p21$^{Cip1}$ mouse SMC exposed to the cGMP analogue 8Br-cGMP. Membranes were subsequently probed for β$^-$-actin to assure equal loading. Results shown are representative of 3 independent experiments. FIG. 5D is a bar graph illustrating [$^3$H]thymidine incorporation of SMC isolated from wild type (wt) and p21$^{Cip1}$ (p21$^{-/-}$) deficient mice in the presence and absence of the cGMP analogue 8Br-cGMP. Results shown are the mean±standard deviation (n=4; *P<0.05 versus air and 8BrcGMP). FIG. 5E is a composite picture of a Western blot of phosphorylated p38 MAPK (p-p38), ATF-2 (p-ATF-2), JNK (p-JNK) and ERK (p-ERK) of SMC exposed to CO (250 ppm). Membranes were subsequently probed with an antibody against total p38 MAPK, ATF-2, JNK and ERK to assure equal loading. Blots are representative of 3 independent experiments. FIG. 5F is a bar graph illustrating [$^3$H] thymidine incorporation in mouse SMC exposed to CO (250 ppm) in the presence and absence of the p38 MAPK inhibitor SB203580. Results shown are the mean±standard deviation from 4 independent experiments (p<0.005; versus air and CO/SB treated cells). FIG. 5G is a composite picture of a Western blot of p21$^{Cip1}$ from mouse SMC exposed to CO (250 ppm) in the presence and absence of the p38 MAPK inhibitor SB203580 or DMSO, used as a vehicle. The same membrane was probed with an antibody against β-actin to assure equal loading. Results shown are representative of 3 independent experiments.

Figure 6A:
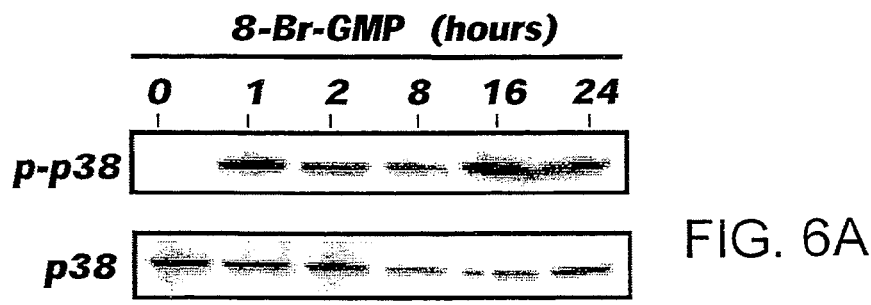
FIG. 6A is a composite picture of a Western blot illustrating the effect of 8-Br-cGMP on expression of p38 MAPK in mouse SMC.
Figure 6B:
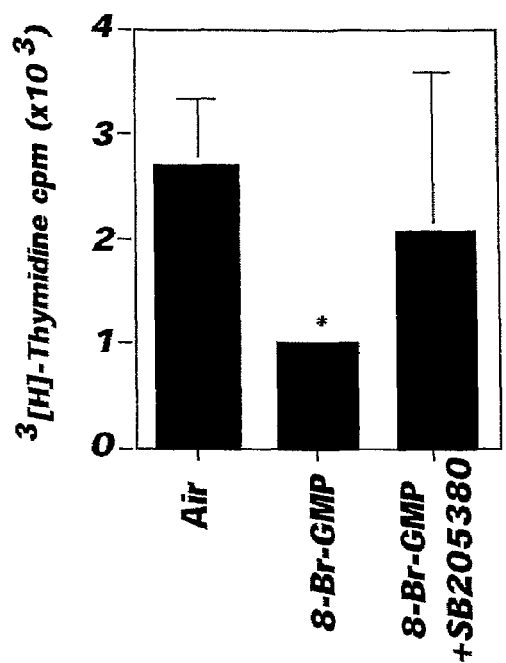
FIG. 6B is a bar graph illustrating [$^3$H]thymidine uptake by mouse SMC exposed to air (Air), CO plus 8-Br-cGMP (8-Br-cGMP), and CO plus 8-Br-cGMP plus SB203580 (8-Br-cGMP+SB203580).

FIGS. 6A-6B illustrate that CO activates p38 MAPK through a mechanism that requires the generation of cGMP. FIG. 6A is a composite picture of a Western blot of phosphorylated p38 MAPK from mouse SMC exposed to the cGMP analogue 8BrcGMP. Membranes were subsequently probed with an antibody against total p38 to assure equal loading. The composite blot shown in FIG. 6A is representative of 3 independent experiments. FIG. 6B is a bar graph illustrating [$^3$H]thymidine incorporation in mouse SMC exposed to CO (250 ppm) in the presence and absence of the cGMP analog 8-BrcGMP. Results shown are the mean±standard deviation from 4 independent experiments.

Figure 10:
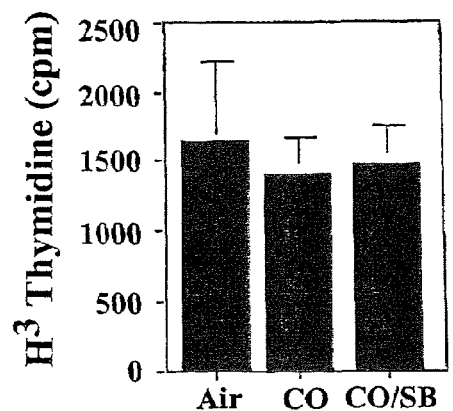
FIG. 10 is a bar graph illustrating [$^3$H]thymidine uptake by p21$^{-/-}$ mouse-derived SMC treated with air (Air), CO (250 ppm; CO) and CO plus SB203580 (CO/SB).

FIG. 10 is a bar graph illustrating that CO does not suppress proliferation in SMC from p21$^{-/-}$ mice. The bar graph presents the results of a [$^3$H]thymidine incorporation assay to assess cellular proliferation (counts per minute; cpm) in SMC derived from p21$^{-/-}$ mice treated with CO (250 ppm) in the presence and absence of the p38 MAPK inhibitor SB203580 (SB).

Exposure of SMC to CO increased intracellular cGMP levels (FIG. 5A). The ability of CO to suppress SMC proliferation and to up-regulate p21$^{Cip1}$ expression was impaired under inhibition of guanylate cyclase activity by 1H(1,2,4) Oxadiazolo(4,3-a) Quinoxalin-1 (ODQ) (FIG. 5B). The non-degradable cGMP analogue 8-Bromoguanosine 3'-5'-cyclic monophosphate sodium salt (8-Br-cGMP) suppressed SMC proliferation (FIG. 5D) and increased expression of p21$^{Cip1}$ comparably to CO (FIG. 5C). Suppression of proliferation by 8-Br-cGMP was impaired in SMC derived from p21$^{-/-}$ mice (FIG. 5D). It thus appears that the anti-proliferative effect of CO is mediated via activation of guanylate cyclase, accumulation of cGMP and expression/activation of p21$^{Cip1}$. Activation of cGMP dependent kinases (PKG α and β) seems to be required for CO to suppress SMC proliferation since an inhibitor of PKG abrogated the anti-proliferative effect of CO.

Whether the anti-proliferative effect of CO in SMC involved the activation of the p38 MAPK signal transduction pathway was investigated. CO activated p38 MAPK in SMC (FIG. 5E), as it does in endothelial cells and monocytes/macrophages. p38 MAPK phosphorylation/activation peaked four hours after exposure to CO and returned to basal levels thereafter (FIG. 5E). Exposure of SMC to CO was also associated with the activation of ATF-2, a transcription factor most often activated through the p38 MAPK signal transduction pathway (FIG. 5E). Inhibition of p38 MAPK activation by the pyridinyl imidazol SB203580, a selective inhibitor of the p38α and β isoforms, blocked the ability of CO to up-regulate expression of p21$^{Cip1}$ (FIG. 5G) and suppressed the anti-proliferative effect of CO (FIG. 5F). Additionally, CO did not inhibit proliferation in cells isolated from mice deficient in mitogen activated protein kinase kinase 3 (mkk3$^{-/-}$), the upstream kinase that activates p38α and p38β. SB203580 did not modulate the effects of CO on proliferation of SMC from p21$^{-/-}$ mice (FIG. 10). These data indicate that p38 MAPK activation is critical for upregulation of p21$^{Cip1}$ and inhibition of SMC proliferation by CO. CO did not modulate activation of extra-cellular regulated kinases 1 and 2 (ERK-1 and -2) (FIG. 5E), indicating that this signal transduction pathway is not involved in the anti-proliferative effect of CO. CO induced activation of jun-activated kinases 1 and 2 (JNK-1 and -2) (FIG. 5E).

Given that CO induces the generation of cGMP (FIG. 5A) and activation of p38 MAPK (FIG. 5E) in SMC, the interrelationship between these two signal transduction pathways was investigated. Activation of p38 MAPK by CO was abolished when the generation of cGMP was blocked by ODQ. Exposure of SMC to 8-bromo-cGMP activated p38 MAPK (FIG. 6A) and the anti-proliferative effect of 8Br-cGMP was abrogated in the presence of SB203580 (FIG. 6B). Consistent with these findings, the ability of 8Br-cGMP to up-regulate the expression of $p21^{Cip1}$ was suppressed by SB203580.

The Anti-Proliferative Effect of CO does not Require Expression of Nitric Oxide Synthases.

Figure 11A:
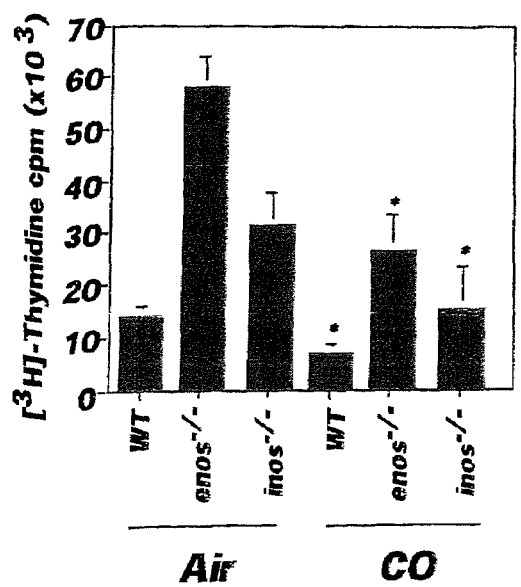
FIG. 11A is a bar graph illustrating [$^3$H]thymidine uptake by wild type (wt), enos$^{-/-}$, and inos$^{-/-}$ deficient mouse-derived SMC exposed to air (Air) or CO (250 ppm; CO).
Figure 11B:
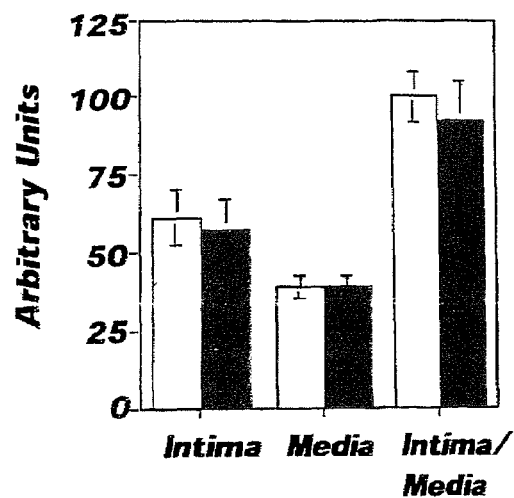
FIG. 11B is a bar graph illustrating the mean intimal and media areas, and the intima/media area ratios, of carotid arteries from Sprague-Dawley rats exposed to room air (white bars) or NO (Black bars; 1 hour; 250 ppm) prior to balloon injury of the carotid artery.

FIGS. 11A-11B illustrate that NO is not involved with the anti-proliferative effect of CO. FIG. 11A is a bar graph illustrating [$^3$H]thymidine incorporation in mouse SMC isolated from wild type (wt) and enos$^{-/-}$ and inos$^{-/-}$ deficient mice in the presence and absence of CO (250 ppm). Results shown are the mean±standard deviation (n=6-8, *P<0.001 versus wt). FIG. 11B is a bar graph illustrating the mean intimal and media areas of carotid arteries from Sprague-Dawley rats exposed to room air (white bars) or NO (Black bars; 1 hour; 250 ppm) before balloon injury of the carotid artery. All animals were exposed to room air following injury. Two weeks after injury carotid arteries were removed, sectioned and stained with hematoxylin and eosin (H&E). Areas corresponding to the intimal and media regions were calculated. Results are the mean±standard deviation from representative 40 sections taken from 3 rats per treatment group.

SMC exposed to CO (250 or 10,000 ppm) for varying amounts of time showed no induction of either NOS isoform by western blotting. SMC from mice deficient for the constitutive/endothelial isoform of nitric oxide synthase (eNOS/NOS-3; nos-3$^{-/-}$) or the inducible isoform (iNOS/NOS-2; nos-2$^{-/-}$) showed a significantly greater uptake of thymidine when exposed to serum as compared to SMC derived from wild type mice (FIG. 11A). Exposure to CO significantly inhibited proliferation of SMC derived from wild type, nos-2$^{-/-}$ or nos-3$^{-/-}$ mice (51±12.9% and 51±25% and 54±11% inhibition respectively; p<0.001 versus air treated controls) (FIG. 11A). These data indicate that the anti-proliferative effect of CO can occur in the absence of iNOS or eNOS. Similarly, under similar conditions to the ones used for CO (250 ppm; one hour pre-treatment), NO did not modulate intimal thickening triggered by balloon injury. NO administered at 500 ppm was lethal.

CO does not Inhibit the Expression of the Plasminogen Activator Inhibitor Type 1 (PAI-1) in SMC.

Figures 12A, 12B, 12C:
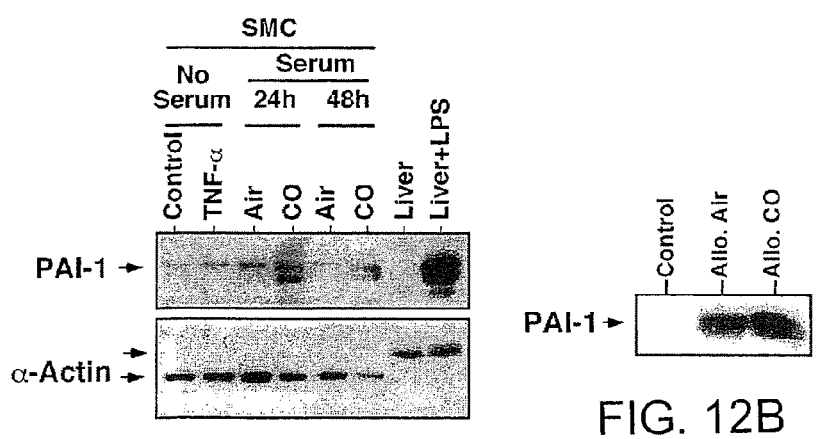
FIG. 12A is a composite picture of a Western blot illustrating PAI-1 expression in SMC treated with and without serum (Serum and No Serum, respectively) and with and without CO (Air and CO, respectively) for 24 or 48 hours. Liver=whole cell lysates from rat liver homogenates treated without endotoxin (LPS). Liver+LPS=whole cell lysates from rat liver homogenates treated with endotoxin (LPS). TNF-α=control wherein TNF-α was added to the cell culture to stimulate expression of PAI-1.
FIG. 12B is a picture of a Western blot illustrating PAI-1 expression in untransplanted (control), transplanted (Allo.+Air), and CO-treated transplanted (Allo.+CO) aortas 56 days after transplantation.
FIG. 12C is a picture of a Commassie blue stained polyacrylamide gel used for the Western blot of FIG. 12B, which illustrates PAI-expression in untransplanted (control), transplanted (Allo.+Air), and CO-treated transplanted (Allo.+CO) aortas 56 days after transplantation.

FIGS. 12A, 12B and 12C illustrate that CO increases PAI-1 protein expression levels. FIG. 12A is a composite picture of a Western blot analysis for PAI-1 in SMC treated with and without CO (250 ppm) for 24 or 48 hours. Whole cell lysates from rat liver homogenates treated with and without endotoxin (LPS) were used as controls. α-actin was used to assay protein loading. FIG. 12B is a composite picture of a Western blot analysis for PAI-1 in untransplanted (control), transplanted (Allo.+Air), and CO-treated transplanted (Allo.+CO) aortas after 56 days. FIG. 12C is the Commassie blue-stained polyacrylamide gel used to create the Western blot of FIG. 12B, and illustrates that the same amount of protein is loaded in each lane.

CO suppresses expression of PAI-1 in Mø, which is key to the protective effect of CO in preventing lung ischemia reperfusion injury in mice. Exposure of SMC to serum did not alter expression of PAI-1 by western blot (FIG. 12A). CO treatment slightly increased PAI-1 protein, suggesting that the anti-proliferative effect of CO does not involve down-regulation of PAI-1. Similarly, PAI-1 protein expression in allogeneic aortas transplanted under CO treatment was similar to that of allogeneic aortas transplanted in the absence of CO as tested by immunohistology and Western blot (FIG. 12B). This suggests that the ability of CO to modulate vascular injury associated with chronic graft rejection might not be directly linked to the expression of PAI-1.

CO is generated physiologically in most cell types through the catabolism of heme by enzymes of the heme oxygenase family. Expression of the inducible enzyme, HO-1, is a protective response to injury that limits the deleterious effects associated with inflammatory reactions. The protective effects of HO-1 are wide-ranging, including inhibition of the development of atherogenesis and intimal hyperplasia, and can in many instances be mimicked by CO. The present studies demonstrate that CO possesses direct vasoprotective properties. Continuous exposure to low concentration of CO (250 ppm) suppresses development of intimal hyperplasia and graft infiltration by activated leukocytes (FIGS. 1A-1I and 2A-2C) associated with transplant arteriosclerosis (FIG. 1A-1I). Exposure to CO (250 ppm) for just one hour prior to injury suppresses the intimal hyperplasia associated with carotid artery angioplasty injury in rats (FIGS. 3A-3G).

The physiologic relevance of the anti-proliferative effect of HO-1 in SMC, originally described in pulmonary epithelial cells, is supported by the observation that SMC from HO-1 deficient mice proliferate more rapidly in vitro and in vivo than wild type SMC. The present data demonstrate that CO suppresses SMC proliferation in a manner similar to HO-1.

Generation of cGMP and the expression of $p21^{Cip1}$ are essential for the effects of CO, and are interrelated. The ability of CO to up-regulate $p21^{Cip1}$ expression and suppress SMC proliferation is dependent on activation of guanylate cyclase (FIGS. 5A-5G). CO up-regulates $p21^{Cip1}$ (FIGS. 4A-4F) and the anti-proliferative effect of CO is dependent on the expression of $p21^{Cip1}$ as this effect is abrogated in $p21^{Cip1-/-}$ SMC (FIGS. 6A-6B). The ability of 8-Br-cGMP to suppress SMC proliferation was impaired in SMC derived from $p21^{Cip1}$ deficient mice (FIGS. 5A-5G), suggesting that cGMP suppresses SMC proliferation in vitro via the up-regulation of $p21^{Cip1}$.

The individual contribution of cGMP and p38 MAPK to the effects of CO seems to be cell type specific. The present data demonstrate that the anti-proliferative effect of CO in SMC is dependent on both signal transduction pathways (FIGS. 5A-5G). CO requires cGMP for activation of p38 MAPK, which is needed for CO to up-regulate $p21^{Cip1}$ and suppress SMC proliferation. It is suggested that CO, like NO, activates p38 MAPK via cGMP and activation of cGMP dependent protein kinases, consistent with the observation that inhibition of PKGα and/or β suppresses the anti-proliferative effect of CO. The present data suggest that the anti-proliferative effect of CO is distinct from and can act independently of NO. It should be noted that the link between cGMP, p38 MAPK and $p21^{Cip1}$ has not been reported in cells exposed to HO-1 or CO.

SMC express $p21^{Cip1}$ upon vascular injury and recombinant adenovirus mediated $p21^{Cip1}$ expression in SMC suppresses intimal hyperplasia following vascular injury. The present data show that physiological expression of $p21^{Cip1}$ is involved in intimal hyperplasia: following arterial injury, intimal hyperplasia in $p21^{-/-}$ mice is three times higher as wild type controls (FIG. 4F), strongly supporting the notion that CO induction of $p21^{Cip1}$ expression in SMC (FIG. 5D) contributes to suppress intimal hyperplasia following vascular injury.

$p21^{-/-}$ mice were used to assess the role of $p21^{Cip1}$ expression on the ability of CO to suppress intimal hyperplasia following arterial injury, $p21^{-/-}$ mice. One hour of CO pretreatment was sufficient to suppress by more than 80% the development of intimal hyperplasia in $p21^{-/-}$ mice or wild-type mice, as compared with their respective air-treated controls (FIG. 4F). One interpretation of these data is that the ability of CO to suppress neointimal proliferation in vivo acts independently of $p21^{Cip1}$ in SMC. In mice, in contrast with rats, there is a significant inflammatory/thrombotic process that presumably leads to intimal proliferation. Given the potent anti-inflammatory effects of CO, it also seems possible that CO suppresses intimal hyperplasia in mice by inhibiting inflammation, a process that is almost certainly independent of $p21^{Cip1}$.

Given the known suppression of PAI-1 by CO in monocyte-macrophages and the importance of PAI-1 in the pathogenesis of intimal hyperplasia following vascular injury in some studies, whether a similar suppression of PAI-1 occurred in the present system was investigated. No decrease in the level of PAI-1 protein expression at 56 days after transplantation was observed (FIG. 12B).

Example 2

Protocols for the Treatment of Patients During Angioplasty and Transplantation Procedures The following example illustrates protocols for treating patients during angioplasty procedures and for treating a donor, organ, and/or recipient with carbon monoxide during a transplantation procedure. Any one or more of the following procedures may be used in a given transplantation procedure.

Angioplasty

CO can be administered systemically or locally to a patient prior to, during, and/or after an angioplasty procedure is performed in the patient. Treatment can be administered at doses varying from 10 ppm to 1000 ppm (e.g., about 100 ppm to about 800 ppm, about 150 ppm to about 600 ppm (e.g., about 150 ppm), or about 200 ppm to about 500 ppm (e.g., about 250 ppm or about 500 ppm)). For example, CO can be administered to the patient, intermittently or continuously, starting 0 to 20 days before the procedure is performed, e.g., starting at least about 30 minutes, e.g., about 1, 2, 3, 5, 7, or 10 hours, or about 1, 2, 4, 6, 8, 10, 12, 14, 18, or 20 days, or greater than 20 days, before the procedure. Alternatively or in addition, CO can be administered to the patient during the procedure, e.g., through an instrument used to perform the angioplasty and/or by inhalation. Alternatively or in addition, CO can be administered to the patient after the procedure, e.g., starting immediately after completion of the procedure, and continuing for about 1, 2, 3, 5, 7, or 10 hours, or about 1, 2, 5, 8, 10, 20, 30, 50, or 60 days, or indefinitely, after the completion of the procedure.

Transplantation

Treatment of a Donor

Prior to harvesting an organ or tissue, the donor can be treated with inhaled carbon monoxide (250 ppm) for one hour. Treatment can be administered at doses varying from 10 ppm to 1000 ppm for times varying from one hour to six hours, or for the entire period from the moment when it becomes possible to treat a brain-dead (cadaver) donor to the time the organ is removed. Treatment should start as soon as possible following the declaration that brain death is present. In some applications, it may be desirable to begin treatment before brain death.

For non-human animals (e.g., pigs) to be used as xenotransplantation donors, the live animal can be treated with relatively high levels of inhaled carbon monoxide, as desired, so long as the carboxyhemoglobin so produced does not compromise the viability and function of the organ to be transplanted. For example, one could use levels greater than 500 ppm (e.g., 1000 ppm or higher, and up to 10,000 ppm, particularly for brief times).

Treatment of the Organ In Situ

Before an organ is harvested from a donor, it can be flushed with a solution, e.g., a buffer or medium, without red blood cells while it is still in the donor. The intent is to flush the organ with a solution saturated with carbon monoxide and maintained in a carbon monoxide atmosphere so that the carbon monoxide content remains at saturation. Flushing can take place for a time period of at least 10 minutes, e.g., 1 hour, several hours, or longer. The solution should ideally deliver the highest concentration of carbon monoxide possible to the vasculature of the organ.

Treatment of an Organ or Tissue

The organ or tissue can be preserved in a medium that includes carbon monoxide from the time it is removed from the donor to the time it is transplanted to the recipient. This can be performed by maintaining the organ or tissue in the medium comprising CO, or by perfusing it with such a medium. Since this occurs ex vivo rather than in an animal, very high concentrations of CO gas can be used (e.g., 10,000 ppm) to keep the medium saturated with CO.

Treatment of a Recipient

The recipient can be treated with carbon monoxide. Treatment can begin on any day before the transplantation procedure, e.g., on the day of the transplantation procedure at least one hour before surgery begins. Alternatively, it could begin at least 30 minutes before re-perfusion of the organ in the recipient. It can be continued for at least 30 minutes, e.g., 1 hour. Carbon monoxide doses between 10 ppm and 3000 ppm can be delivered for varying times, e.g., minutes or hours, and can be administered on the day of and on days following transplantation. For example, a recipient can inhale a concentration of carbon monoxide, e.g., 3000 ppm, for three consecutive 10 second breath holds. Alternatively, the recipient can inhale, say 200 ppm for an extended time, such as 20 days. Carboxyhemoglobin concentrations can be utilized as a guide for appropriate administration of carbon monoxide to a patient. Usually, treatments for recipients should not raise carboxyhemoglobin levels above those considered to pose an acceptable risk for a patient in need of a transplant.

A number of embodiments of the invention have been described. Nevertheless, it will be understood that various modifications may be made without departing from the spirit and scope of the invention. Accordingly, other embodiments are within the scope of the following claims.

What is claimed is:

1. A kit comprising:
    (a) an angioplasty device; and
    (b) a vessel containing a carbon monoxide composition.
2. The kit of claim 1, wherein the angioplasty device is capable of administering carbon monoxide to a patient.
3. The kit of claim 1, further comprising:
    (c) instructions for use of the carbon monoxide composition in a method for performing angioplasty in a patient.
4. The kit of claim 1, wherein the carbon monoxide composition is a liquid composition.

5. The kit of claim 1, wherein the carbon monoxide composition is a gaseous composition.

6. An angioplasty device comprising:

an inflatable member comprising a plurality of apertures; and a reservoir comprising carbon monoxide gas and connected to the inflatable member, whereby the gas is provided to the inflatable member during inflation of the inflatable member.

* * * * *